US012618076B2

(12) United States Patent
Deans

(10) Patent No.: US 12,618,076 B2
(45) Date of Patent: May 5, 2026

(54) METHODS OF ENGINEERING PLATELETS FOR TARGETING CIRCULATING TUMOR CELLS

(71) Applicant: University of Utah Research Foundation, Salt Lake City, UT (US)

(72) Inventor: Tara Deans, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1070 days.

(21) Appl. No.: 17/765,872

(22) PCT Filed: Sep. 30, 2020

(86) PCT No.: PCT/US2020/053445
§ 371 (c)(1),
(2) Date: Apr. 1, 2022

(87) PCT Pub. No.: WO2021/067378
PCT Pub. Date: Apr. 8, 2021

(65) Prior Publication Data
US 2022/0348938 A1     Nov. 3, 2022

Related U.S. Application Data

(60) Provisional application No. 62/908,874, filed on Oct. 1, 2019.

(51) Int. Cl.
| | |
|---|---|
| *C12N 15/63* | (2006.01) |
| *A61K 35/19* | (2015.01) |
| *A61P 35/00* | (2006.01) |
| *C07K 16/30* | (2006.01) |
| *C12N 5/078* | (2010.01) |
| *C12N 15/90* | (2006.01) |

(52) U.S. Cl.
CPC .............. *C12N 15/63* (2013.01); *A61K 35/19* (2013.01); *A61P 35/00* (2018.01); *C07K 16/30* (2013.01); *C12N 5/0644* (2013.01); *C07K 2317/10* (2013.01); *C07K 2317/73* (2013.01); *C07K 2319/55* (2013.01); *C07K 2319/92* (2013.01); *C12N 15/907* (2013.01); *C12N 2310/20* (2017.05); *C12N 2506/02* (2013.01); *C12N 2506/11* (2013.01); *C12N 2510/00* (2013.01)

(58) Field of Classification Search
CPC .. C12N 15/63; C12N 5/0644; C12N 2506/11; A61K 35/19; C07K 2317/73; C07K 19/55; C07K 2319/92
See application file for complete search history.

(56) References Cited

U.S. PATENT DOCUMENTS

| | | | |
|---|---|---|---|
| 7,696,168 B2 | 4/2010 | Kuliopulos et al. | |
| 9,982,034 B2 | 5/2018 | Wilcox et al. | |

| | | | |
|---|---|---|---|
| 2005/0053587 A1 | 3/2005 | Galipeau et al. | |
| 2007/0243608 A1 | 10/2007 | Kyba et al. | |
| 2010/0175141 A1 | 7/2010 | Collins et al. | |
| 2011/0256626 A1 | 10/2011 | Park et al. | |
| 2013/0274129 A1 | 10/2013 | Katzen et al. | |
| 2014/0024118 A1 | 1/2014 | Nakamura et al. | |
| 2014/0086883 A1 | 3/2014 | Poncz et al. | |
| 2014/0315753 A1 | 10/2014 | Guye et al. | |
| 2014/0363455 A1 | 12/2014 | Stull et al. | |
| 2016/0002599 A1* | 1/2016 | Eto ...................... | C12N 5/0644 |
| 2018/0273980 A1 | 9/2018 | Qi et al. | |
| 2019/0010456 A1 | 1/2019 | Deans | |
| 2019/0048317 A1 | 2/2019 | Eto et al. | |

FOREIGN PATENT DOCUMENTS

| | | | | |
|---|---|---|---|---|
| EP | 3312270 A1 | 4/2018 | | |
| WO | WO-1999/043809 A1 | 9/1999 | | |
| WO | WO-2003/072755 A2 | 9/2003 | | |
| WO | WO-2009/137629 A2 | 11/2009 | | |
| WO | WO-2013/045632 | 4/2013 | | |
| WO | WO-2017/011550 A1 | 1/2017 | | |
| WO | WO2017132580 A2 * | 8/2017 | ............. | A61K 47/48 |
| WO | WO2019165444 A1 * | 8/2019 | ............. | C07K 14/47 |

OTHER PUBLICATIONS

Nakamura et al. (2014). "Expandable megakaryocyte cell lines enable clinically applicable generation of platelets from human induced pluripotent stem cells" Cell stem cell, 14(4), 535-548. (Year: 2014).*

Li et al. (2016) "Genetic engineering of platelets to neutralize circulating tumor cells" Journal of Controlled Release, 228, 38-47. (Year: 2016).*

Wang et al. (2018) "Reduction of non-specific toxicity of immunotoxin by intein mediated reconstitution on target cells" International Immunopharmacology, 66, 288-295. (Year: 2018).*

Wang, Jing et al., Reduction of non-specific toxicity of immunotoxin by intein mediated reconstitution on target cells, Int'l. Immunopharmacology, 66:288-295 (2018).

Abe, T. et al., "Effect of recombinant erythropoietin in interaction with stromal factors on cord blood hematopoiesis." Blood. 1996; 87(8):3212-7.

Antonchuk, J. et al., "HOXB4-induced expansion of adult hematopoietic stem cells ex vivo." Cell. 2002; 109(1):39-45.

Assou, S. et al., "Dynamic changes in gene expression during human early embryo development: from fundamental aspects to clinical applications." Hum Reprod Update. 2011; 17(2):272-90 (33 pages).

(Continued)

*Primary Examiner* — James Joseph Graber
(74) *Attorney, Agent, or Firm* — BALLARD SPAHR LLP

(57) ABSTRACT

Disclosed herein are nucleic acid constructs that can be used to build genetic circuits for producing antibodies comprising split toxins. Also disclosed herein are methods of producing platelets comprising the antibodies. The platelets produced by the methods disclosed herein can be used to target circulating tumor cells.

12 Claims, 11 Drawing Sheets

Specification includes a Sequence Listing.

(56)                    References Cited

OTHER PUBLICATIONS

Aulehla, A. and Pourquie, O. "Oscillating signaling pathways during embryonic development." Curr Opin Cell Biol. 2008; 20(6):632-7.

Avanzi, MP, et al. "A novel bioreactor and culture method drives high yields of platelets from stem cells." Transfusion 2016; 56(1): 170-8.

Becskei, A. and Serrano, L., "Engineering stability in gene networks by autoregulation." Nature. 2000; 405(6786):590-3.

Blin, A, et al. "Microfluidic model of the platelet-generating organ: beyond bone marrow biomimetics." Sci Rep 2016; 6: 21700.

Borsig, L. "The role of platelet activation in tumor metastasis." Expert Rev Anticancer Ther 2008; 8(8): 1247-55.

Bouhassira, E.E., "Concise Review: Production of Cultured Red Blood Cells from Stem Cells." Stem Cells Transl Med. 2012; 1(12):927-33.

Bush, L, et al. "Combination image flow cytometry for single-cell analysis reveals novel methods for isolating subsets of megakaryocyte progenitor populations." bioRxiv, doi: 10.1101/512442; Jan. 7, 2019.

Carvajal-Vallejos P., et al., "Unprecedented rates and efficiencies revealed for new natural split inteins from metagenomic sources." J. Biol. Chem. 287: 28686-28696 (2012).

Casola, S., "Mouse Models for miRNA Expression: the ROSA26 Locus." Methods Mol Biol. 2010; 667:145-63.

Caspi, et al., "Distribution of split DnaE inteins in cyanobacteria." Mol Microbiol,. 50: 1569-1577 (2003).

Chang, Y, et al. "From hematopoietic stem cells to platelets." Journal of thrombosis and haemostasis:JTH 2007; 5 Suppl 1: 318-27.

Chen, C.-Y.A. et al., "Versatile applications of transcriptional pulsing to study mRNA turnover in mammalian cells." RNA. 2007; 13(10):1775-86.

Chen, H.-W. et al., "Dynamic changes of gene expression profiles during postnatal development of the heart in mice." Heart. 2004; 90(8):927-34.

Chen, Y.Y. et al., "Genetic control of mammalian T-cell proliferation with synthetic RNA regulatory systems." Proc natl Acad Sci USA. 2010; 107:8531-6.

Chin, J.W., "Programming and engineering biological networks." Curr Opin Struct Biol. 2006; 16:551-6.

Choi J., et al., "Protein trans-splicing and characterization of a split family B-type DNA polymerase from the hyperthermophilic archaeal parasite Nanoarchaeum equitans." J Mol Biol 556: 1093-1106 (2006).

Chubb, J.R. et al., "Transcriptional pulsing of a developmental gene." Curr Biol. 2006; 16(10):1018-25.

Cid, J. and Lozano, M., "Platelet dose for prophylactic platelet transfusions." Expert Rev Hematol. 2010; 3(4):397-400.

Corum, L.E. and Hlady, V., "Screening platelet-surface interactions using negative surface charge gradients." Biomaterials. 2010; 31(12):3148-55.

Corum, L.E. and Hlady, V., "The effect of upstream platelet-fibrinogen interactions on downstream adhesion and activation." Biomaterials. 2012; 33(5):1255-60 (14 pages).

Dassa B., et al., "Trans protein splicing of cyanobacterial split inteins in endogenous and exogenous combinations." Biochemistry, 46:322-330 (2007).

Deans, TL, et al. "Regulating synthetic gene networks in 3D materials." Proceedings of the National Academy of Sciences of the United States of America 2012; 109(38): 15217-22.

Deans, TL, et al. "A tunable genetic switch based on RNAi and repressor proteins for regulating gene expression in mammalian cells." Cell 2007; 130(2): 363-72.

Deans, TL, and Elisseeff, JH. "Stem cells in musculoskeletal engineered tissue." Current opinion in biotechnology 2009; 20(5): 537-44.

Deans, TL, and Elisseeff, JH. The life of a cell: probing the complex relationships with the world. Cell Stem Cell 2010; 6(6): 499-501.

Deutsch, VR, and Tomer, A. "Megakaryocyte development and platelet production." British journal of haematology 2006; 134(5): 453-66.

Diaz, LA, Jr., et al. "The molecular evolution of acquired resistance to targeted EGFR blockade in colorectal cancers." Nature 2012; 486(7404): 537-40.

Di Buduo, CA, et al. "Programmable 3D silk bone marrow niche for platelet generation ex vivo and modeling of megakaryopoiesis pathologies." Blood 2015; 125(14): 2254-64.

El Golli, N, et al. "Evidence for a granule targeting sequence within platelet factor 4." The Journal of biological chemistry 2005; 280(34): 30329-35.

Elowitz, M.B. and Leibler, S., "A synthetic oscillatory network of transcriptional regulators." Nature. 2000; 403(6767):335-8.

Erpenbeck L, and Schon MP. "Deadly allies: the fatal interplay between platelets and metastasizing cancer cells." Blood 2010; 115(17): 3427-36.

Feng, Q. et al., "Scalable generation of universal platelets from human induced pluripotent stem cells." Stem Cell Reports. 2014; 3:817-31.

Fitzgerald M, et al. "Adoption of the Q Transcriptional System for Regulating Gene Expression in Stem Cells." ACS synthetic biology 2017; 6(11): 2014-20.

Fitzgerald M, et al. "Rosa26 docking sites for investigating genetic circuit silencing in stem cells." Synthetic Biology 2020; 5(1):ysaa014.

Friedland, A.E., et al., "Synthetic gene networks that count." Science. 2009; 324:1199-202.

Fugger, L et al., "From genes to function: the next challenge to understanding multiple sclerosis." Nat Rev Immunol. 2009; 9(6):408-17.

Fujimoto, T.T. et al., "Production of functional platelets by differentiated embryonic stem (ES) cells in vitro." Blood. 2003; 102(12):4044-51.

Gardner, T.S. et al., "Construction of a genetic toggle switch in Escherichia coli." Nature. 2000; 403:339-42.

Gay, LJ, and Felding-Habermann, B. "Contribution of platelets to tumour metastasis." Nat Rev Cancer 2011; 11(2): 123-34.

Gkountela, S, et al. "Recent advances in the biology of human circulating tumour cells and metastasis." ESMO Open 2016; 1(4): e000078.

Grayson, W.L. et al., "Effects of initial seeding density and fluid perfusion rate on formation of tissue-engineered bone." Tissue Eng Part A. 2008; 14(11): 1809-20.

Grover, A. et al., "Erythropoietin guides multipotent hematopoietic progenitor cells toward an erythroid fate." J Exper Med. 2014; 211:181-8.

Gutierrez, L. et al., "Ablation of Gata1 in adult mice results in aplastic crisis, revealing its essential role in steady-state and stress erythropoiesis." Blood. 2008; 111(8):4375-85.

Handwerger, S. and Aronow, B., Dynamic changes in gene expression during human trophoblast differentiation. Recent Prog Horm Res. 2003; 58:263-81.

Haugh, M.G. et al., "Temporal and spatial changes in cartilage-matrix-specific gene expression in mesenchymal stem cells in response to dynamic compression." Tissue Eng Part A. 2011; 17(23-24):3085-93.

Hippenmeyer, S. et al., "Genetic mosaic dissection of Lis1 and Ndel1 in neuronal migration." Neuron. 2010; 68(4):695-709 (27 pages).

Holland, A.J. et al., "Inducible, Reversible System for the Rapid and Complete Degradation of Proteins in Mammalian Cells." Proc Natl Acad Sci USA. 2012; 109(49):E3350-7.

Holmes, ML, et al. "Cloning and analysis of the thrombopoietin-induced megakaryocyte-specific glycoprotein VI promoter and its regulation by GATA-1, Fli-1, and Sp1". The Journal of Biological Chemistry. Dec. 13, 2002, vol. 277, No. 50, pp. 48333-48341.

Honn, KV, et al. "Platelets and cancer metastasis: a causal relationship?" Cancer Metastasis Rev 1992; 11(3-4): 325-51.

Iwasaki, H. et al., "GATA-1 converts lymphoid and myelomonocytic progenitors into the megakaryocyte/erythrocyte lineages." Immunity. 2003; 19(3):451-62.

(56)         References Cited

OTHER PUBLICATIONS

Iyer-Biswas, S. et al., "Stochasticity of gene products from transcriptional pulsing." Phys Rev E Stat Nonlin Soft Matter Phys. 2009; 79(3 Pt 1):031911.

Ito, Y, et al. "Turbulence Activates Platelet Biogenesis to Enable Clinical Scale Ex Vivo Production." Cell 2018; 174(3): 636-48 e18.

Iwai I., et al., "Highly efficient protein trans-splicing by a naturally split DnaE intein from Nostoc punctiforme." FEBS Letters 550: 1853-1858 (2006).

Katzman, R.L. et al., "Collagen-induced platelet aggregation: involvement of an active glycopeptide fragment (alpha1-CB5)." Science. 1973; 181(4100):670-2.

Kaufman, R.M. et al., "Circulating megakaryocytes and platelet release in the lung." Blood. 1965; 26(6):720-31.

Klimchenko, O. et al., "A common bipotent progenitor generates the erythroid and megakaryocyte lineages in embryonic stem cell-derived primitive hematopoiesis." Blood. 2009; 114:1506-17.

Kotula, J.W. et al., "Programmable bacteria detect and record an environmental signal in the mammalian gut." Proc Natl Acad Sci USA. 2014; 111:4838-43.

Kuter, D.J. et al., "Evaluation of bone marrow reticulin formation in chronic immune thrombocytopenia patients treated with romiplostim." Blood. 2009; 114(18):3748-56.

Kuter, DJ. "Biology and chemistry of thrombopoietic agents." Seminars in hematology 2010; 47(3): 243-8.

Kyba, M. et al., "HoxB4 confers definitive lymphoid-myeloid engraftment potential on embryonic stem cell and yolk sac hematopoietic progenitors." Cell. 2002; 109(1):29-37.

Labelle, M, and Hynes, RO. "The initial hours of metastasis: the importance of cooperative host-tumor cell interactions during hematogenous dissemination." Cancer Discov 2012; 2(12): 1091-9.

Lenz, HjJ. "Pharmacogenomics and colorectal cancer. Advances in experimental medicine and biology." 2006; 587: 211-31.

Li, N. "Platelets in cancer metastasis: To help the "villain" to do evil." Int J Cancer 2016; 138(9): 2078-87.

Liu X. and Yang J., "Split dnaE genes encoding multiple novel inteins in Trichodesmium erythraeum." J Biol Chem., 278(29):26315-26318 (2003).

Lo, M.Y. et al., "Rapid transcriptional pulsing dynamics of high expressing retroviral transgenes in embryonic stem cells." PloS One. 2012; 7(5):e37130.

Lopez, A.J. et al., "Promoter-Specific Effects of DREADD Modulation on Hippocampal Synaptic Plasticity and Memory Formation." J. Neurosci. 2016; 36(12):3588-3599.

Lou, XL, et al. "Interaction between circulating cancer cells and platelets: clinical implication." Chin J Cancer Res 2015; 27(5): 450-60.

Love, RR, e al. "Side effects and emotional distress during cancer chemotherapy." Cancer 1989; 63(3): 604-12.

Lu, S.-J. et al., "Platelets generated from human embryonic stem cells are functional in vitro and in the microcirculation of living mice." Cell Res. 2011; 21:530-45.

Lu, T.K. et al., "Next-generation synthetic gene networks." Nat Biotechnol. 2009; 27:1139-50.

Machlus, KR, and Italiano, JE, Jr. "The incredible journey: From megakaryocyte development to platelet formation." The Journal of cell biology 2013; 201(6): 785-96.

Messerle, M. et al., "Dynamic changes in gene expression during in vitro differentiation of mouse embryonic stem cells." Cytokines Mob Ther. 1995; 1(2):139-43.

Metcalf, D., "Hematopoietic cytokines." Blood. 2008; 111:485-91.

Mikhailidis, D.P. et al., "Fibrinogen mediated activation of platelet aggregation and thromboxane A2 release: pathological implications in vascular disease." J Clin Pathol. 1985; 38(10):1166-71.

Miller, J.L. et al., "von Willebrand factor binds to platelets and induces aggregation in platelet-type but not type IIB von Willebrand disease." J Clin Invest. 1983; 72(5):1532-42.

Misale, S, et al. "Emergence of KRAS mutations and acquired resistance to anti-EGFR therapy in colorectal cancer." Nature 2012; 486(7404): 532-6.

Mok, P.-L. et al., "In vitro expression of erythropoietin by transfected human mesenchymal stromal cells." Cytotherapy. 2008; 10(2):116-24.

Mootz, HD, and Muir, TW. "Protein splicing triggered by a small molecule." Journal of the American Chemical Society, 2002; 124(31): 9044-5.

Morrison SJ, et al. "The biology of hematopoietic stem cells." Annual review of cell and Developmental biology 1995; 11: 35-71.

Mosaad, YM. "Hematopoietic stem cells: an overview." Transfusion and apheresis science: official journal of the World Apheresis Association: official journal of the European Society for Haemapheresis 2014; 51(3): 68-82.

Muggli, R., "Collagen-induced platelet aggregation: native collagen quaternary structure is not an essential structural requirement." Thromb Res. 1978; 13(5):829-43.

Mukherji, S. and Van Oudenaarden, A., "Synthetic biology: understanding biological design from synthetic circuits." Nat Rev Genet. 2009; 10(12):859-71.

Nakagawa, Y, et al. "Two differential flows in a bioreactor promoted platelet generation from human pluripotent stem cell-derived megakaryocytes." Exp Hematol 2013; 41(8): 742-8.

Nakamura, S, et al. "Expandable megakaryocyte cell lines enable clinically applicable generation of platelets from human induced pluripotent stem cells." Cell Stem Cell 2014; 14(4): 535-48.

Nhlbi, Stem Cell-Derived Blood Products for Therapeutic Use, RFA-HL-15-022 (2014) (20 pages).

Nishimura, K. et al., "An auxinbased degron system for the rapid depletion of proteins in nonplant cells." Nat Methods. 2009; 6(12):917-22.

Nogami S, et al. "Probing novel elements for protein splicing in the yeast Vma1 protozyme: a study of replacement mutagenesis and intragenic suppression." Genetics 1997; 147(1): 73-85.

Nguyen, H.G. et al., "Conditional overexpression of transgenes in megakaryocytes and platelets in vivo." Blood. 2005; 106(5):1559-1564.

Olsen, A.L., "Designer Blood: Creating Hematopoetic Lineages from Embryonic Stem Cells." Blood. 2006; 107(4):1265-75.

Ono, Y. et al., "Induction of functional platelets from mouse and human fibroblasts by p45NFE2/Maf." Blood. 2012; 120(18):3812-21.

Orkin, S.H. and Zon, L.I., "Hematopoiesis: an evolving paradigm for stem cell biology." Cell. 2008; 132(4):631-44.

Perler, FB. "Protein splicing mechanisms and applications." IUBMB Life 2005; 57(7): 469-76.

Potter, C.J. et al., "The Q system: a repressible binary system for transgene expression, lineage tracing, and mosaic analysis." Cell. 2010; 141(3):536-48.

Ramakrishnan, V. et al., "A thrombin receptor function for platelet glycoprotein Ib-IX unmasked by cleavage of glycoprotein V." Proc Natl Acad Sci USA. 2001; 98(4):1823-8.

Rhee, JM, et al. "In vivo imaging and differential localization of lipid-modified GFP-variant fusions in embryonic stem cells and mice." Genesis 2006; 44(4): 202-18.

Robert, A. et al., "Megakaryocyte and platelet production from human cord blood stem cells." Methods Mol Biol. 2012; 788:219-47.

Schwartz, EC, et al. "Post-translational enzyme activation in an animal via optimized conditional protein splicing." Nature chemical biology 2007; 3(1): 50-4.

Scott, AM, et al. "Monoclonal antibodies in cancer therapy." Cancer Immun 2012; 12: 14.

Selgrade, DF, et al. "Protein scaffold-activated protein trans-splicing in mammalian cells." Journal of the American Chemical Society 2013; 135(20): 7713-9.

Shah N.H., et al., "Naturally split inteins assemble through a "capture and collapse" mechanism." J. Amer. Chem. Soc. 135: 18673-18681.

Singh, A, et al. "Photomodulation of Cellular Gene Expression in Hydrogels." Acs Macro Letters, 2013; 2(3): 269-72.

Siuti, P., et al., "Synthetic circuits integrating logic and memory in living cells." Nature Biotechnol. 2013; 31:448-52.

(56)  References Cited

OTHER PUBLICATIONS

Slusarczyk, A.L. et al., "Foundations for the design and implementation of synthetic genetic circuits." Nature Rev. Genetics. 2012; 13(6):406-20.

Stegner D, et al. "Mechanistic explanation for platelet contribution to cancer metastasis." Thrombosis research 2014; 133 Suppl 2: S149-57.

Sternberg, N. and Hamilton, D., "Bacteriophage P1 site-specific recombination. I. Recombination between loxP sites." J Mol Biol. 1981; 150(4):467-86.

Stetler-Stevenson, M. et al., "Diagnostic utility of flow cytometric immunophenotyping in myelodysplastic syndrome." Blood. 2001; 98(4):79-87.

Subedi, A. et al., "Adoption of the Q transcriptional regulatory system for zebrafish transgenesis." Methods. 2014; 66(3):433-40.

Suzuki, M. et al., "Differential Contribution of the Gatal Gene Hematopoietic Enhancer to Erythroid Differentiation." Mol Cell Biol. 2009; 29(5):1163-75.

Suzuki, N. et al., "Oscillatory protein expression dynamics endows stem cells with robust differentiation potential." PloS One. 2011; 6(11):e27232.

Takayama, N. et al., "Generation of functional platelets from human embryonic stem cells in vitro via ES-sacs, VEGF—promoted structures that concentrate hematopoietic progenitors." Blood. 2008; 111(11):5298-306.

Tasic, B. et al., "Site-specific integrase-mediated transgenesis in mice via pronuclear injection." Proc Natl Acad Sci USA. 2011; 108:7902-7.

Thon, JN, et al. "Cytoskeletal mechanics of proplatelet maturation and platelet release." The Journal of cell biology 2010; 191(4): 861-74.

Tyszkiewicz, AB, and Muir, Tw. "Activation of protein splicing with light in yeast." Nature methods 2008; 5(4): 303-5.

Ungerer, M. et al., "Generation of functional culture-derived platelets from CD34+ progenitor cells to study transgenes in the platelet environment." Circ Res. 2004; 95(5):e36-44.

Ward, Y, et al. "Platelets Promote Metastasis via Binding Tumor CD97 Leading to Bidirectional Signaling that Coordinates Transendothelial Migration." Cell Rep 2018; 23(3): 808-22.

Weisenberger, MS, and Deans, TL. "Bottom-up approaches in synthetic biology and biomaterials for tissue engineering applications." J Ind Microbiol Biotechnol 2018; 45(7): 599-614.

Westrick, R.J. et al., "Murine models of vascular thrombosis (Eitzman series)." Arterioscler Thromb Vasc Biol. 2007; 27(10):2079-93.

Wilcox, D.A. et al., "Integrin αIIb promoter-targeted expression of gene products in megakaryocytes derived from retrovirus-transduced human hematopoietic cells." Proc. Natl. Acad. Sci. USA. 1999; 96:9654-9659.

Wong, S, et al. Simultaneous assembly of two target proteins using split inteins for live cell imaging. Protein Eng Des Sel 2013; 26(3): 207-13.

Wu, N. et al., "Comparison of mouse matrix metalloproteinase 13 expression in free-electron laser and scalpel incisions during wound healing." J Invest Dermatol. 2003; 121(4):926-32.

Wu H., et al., "Protein trans-splicing by a split intein encoded in a split DnaE gene of *synechocystis* sp. PCC6803." Proc Natl Acad Sci USA. 95:9226-9231 (1998).

Xie, Z. et al., "Multi-input RNAi-Based Logic Circuit for Identification of Specific Cancer Cells." Science. 2011; 333(6047):1307-11.

Ye, H. and Fussenegger, M., "Synthetic Therapeutic Gene Circuits in Mammalian Cells." FEBS Letters. 2014; 588(15):2537-44.

Yu, LX, et al. "Platelets promote tumour metastasis via interaction between TLR4 and tumour cell released high-mobility group box1 protein." Nature communications 2014; 5: 5256.

Zeidler, MP, et al. "Temperature-sensitive control of protein activity by conditionally splicing inteins." Nature biotechnology 2004; 22(7): 871-6.

Zettler J., et al., "The naturally split Npu DnaE intein exhibits an extraordinarily high rate in the protein trans-splicing reaction." FEBS Letters, 583:909-914 (2009).

Zhang, C., et al. "Activation of the megakaryocyte-specific gene platelet basic protein (PBP) by the Ets family factor PU.1." The Journal of Biological Chemistry. Oct. 17, 1997, vol. 272, No. 42, pp. 26236-26246.

Zon, L.I., "Intrinsic and extrinsic control of haematopoietic stem-cell self-renewal." Nature. 2008; 453(7193):306-13.

International Search Report and Written Opinion mailed on Oct. 28, 2016 by the International Searching Authority for Patent Application No. PCT/US2016/042084, which was filed on Jul. 13, 2016 and published as WO 2017/011550 on Jan. 19, 2017 (Inventor—Tara L. Deans; Applicant—University of Utah Research Foundation) (19 pages).

International Preliminary Report on Patentability issued on Jan. 16, 2018 by the International Searching Authority for Patent Application No. PCT/US2016/042084, which was filed on Jul. 13, 2016 and published as WO 2017/011550 on Jan. 19, 2017 (Inventor—Tara L. Deans; Applicant—University of Utah Research Foundation) (17 pages).

International Search report and Written Opinion mailed on Dec. 27, 2019 by the International Searching Authority for Patent Application No. PCT/US2019/054032, which was filed on Oct. 1, 2019 and published as WO 2020/072471 on Apr. 9, 2020 (Inventor—Deans; Applicant—University of Utah Research Foundation) (25 pages).

International Preliminary Report on Patentability issued on Mar. 23, 2021 by the International Searching Authority for Patent Application No. PCT/US2019/054032, which was filed on Oct. 1, 2019 and published as WO 2020/072471 on Apr. 9, 2020 (Inventor—Deans; Applicant—University of Utah Research Foundation) (12 pages).

International Search Report and Written Opinion were mailed on Feb. 9, 2021 by the International Searching Authority for International Application No. PCT/US2020/053445, filed on Sep. 30, 2020 (Applicant—University of Utah Research Foundation) (15 Pages).

* cited by examiner

A.

Rosa26
target gene

CRISPR/Cas9 mediated
double stranded break

Rosa26
target gene

Add donor
attP sequence

Homologous
recombination

Rosa26
target gene

C. Confirming integration of docking site

F Primer          Docking site

R Primer

B.

attB donor mini circles

Attachment site

Rosa26
target gene phiC31 integra

Recombination attL          attR          Rosa26
target gene

A.

Intron with
lacO sites

Intron with
lacO sites

B.

Bright Field           Fluorescence
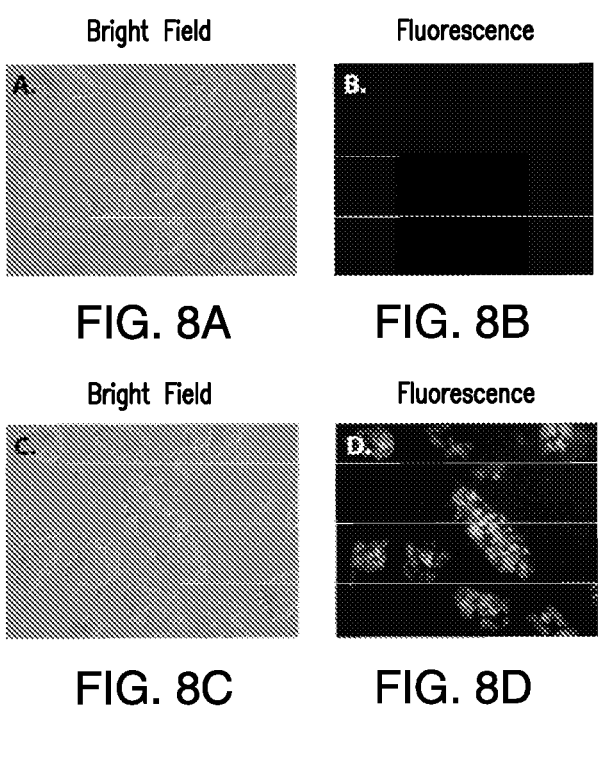
FIG. 8A          FIG. 8B
Bright Field           Fluorescence
FIG. 8C          FIG. 8D
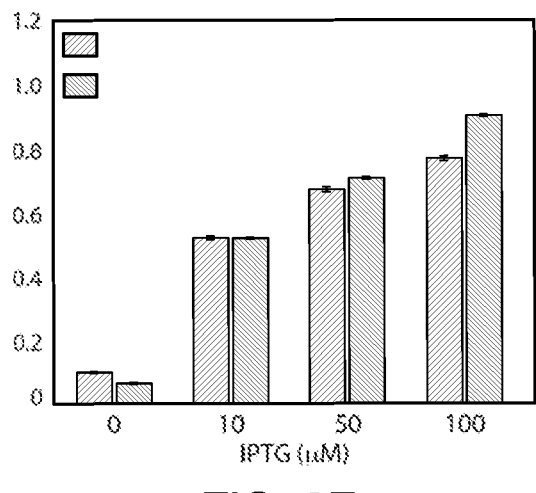
FIG. 8E

F.

SEQUENCE LISTING

```
<160> NUMBER OF SEQ ID NOS: 1

<210> SEQ ID NO 1

<211> LENGTH: 4

<212> TYPE: PRT

<213> ORGANISM: Artificial Sequence

<220> FEATURE:

<223> OTHER INFORMATION: Synthetic construct

<400> SEQUENCE: 1

Leu Lys Asn Gly
1
```

METHODS OF ENGINEERING PLATELETS FOR TARGETING CIRCULATING TUMOR CELLS

CROSS REFERENCE TO RELATED APPLICATIONS

This application claims the benefit of priority under 35 U.S.C. § 371 of International Application No. PCT/US2020/053445, filed on Sep. 30, 2020, which claims the benefit of the filing date of U.S. Provisional Application No. 62/908,874, which was filed on Oct. 1, 2019. The content of this these earlier filed applications is hereby incorporated by reference herein in its entirety.

INCORPORATION OF THE SEQUENCE LISTING

The present application contains a sequence listing that was submitted in ASCII format via EFS-Web concurrent with the filing of the application, containing the file name 21101_0376U2_SL.txt, which is 470 bytes in size, created on Mar. 24, 2022, and is herein incorporated by reference in its entirety pursuant to 37 C.F.R. § 1.52(e)(5).

BACKGROUND

Cancer is the second leading cause of death in the United States. Every year, more than a million people are diagnosed with cancer and more than half a million people succumb to the disease (Society A C. Atlanta: 2012). More than 90% of cancer-associated deaths are caused by metastasis (Lou X L, et al., *Chin J Cancer Res* 2015; 27(5): 450-60). Although cancer continues to be a highly active research area, curative treatments remain elusive. A fundamental challenge in treating patients diagnosed with cancer is preventing metastasis because once cancer spreads, it is difficult to control (Gay L J, Felding-Habermann B. *Nat Rev Cancer* 2011; 11(2): 123-34). Current treatments for metastatic cancer generally require systemic therapy, such as chemotherapy, with the goal of stopping or slowing the growth of cancer or to relieve symptoms caused by it (Gkountela S, et al., *ESMO Open* 2016; 1(4): e000078). Systemic treatments are harsh for many patients because they can cause other health problems including nausea, vomiting, neuropathy, organ and tissue damage, and immune deficiencies (Love R R, et al., *Cancer* 1989; 63(3): 604-12). Similarly, patients using targeted drugs invariably face relapse and develop drug resistance, mostly due to the activation of alternative pathways (Diaz L A, Jr., et al. *Nature* 2012; 486(7404): 537-40; and Misale S, et al. *Nature* 2012; 486(7404): 532-6). Additionally, due to the varying level of cancer specific biomarker expression between patients, drugs that are effective for some patients may be ineffective or have severe side effects for others (Lenz H J. *Advances in experimental medicine and biology* 2006; 587: 211-31). Therefore, therapies that can adapt to different patients and eradicate a wide range of tumor cells while avoiding systemic side effects are highly desirable.

SUMMARY

Disclosed herein are nucleic acid constructs comprising: a) a promoter operatively linked to: i) a first recombination site; ii) c-MYC, BMI1, and BCL-XL; and iii) a second recombination site; and b) a sequence capable of encoding an engineered antibody sequence, wherein the engineered antibody sequence comprises a split toxin sequence flanked by an intein sequence, and wherein the sequence capable of encoding the engineered antibody sequence is out of frame from the promoter.

Disclosed herein are megakaryocytes comprising a nucleic acid construct, wherein the nucleic acid construct comprises a promoter operatively linked to: i) a first recombination site; ii) a second recombination site; and iii) a sequence capable of encoding an engineered antibody sequence, wherein the engineered antibody sequence comprises a split toxin sequence flanked by an intein sequence, wherein the sequence capable of encoding the engineered antibody sequence is in frame with the promoter.

Disclosed herein are engineered megakaryocytes comprising: a) an engineered antibody comprising an Fc region comprising a split toxin sequence flanked by an intein fragment, wherein the intein fragment comprises an intein N-fragment, and wherein the split toxin sequence is N-terminal to an intein N-fragment; b) an engineered antibody comprising an Fc region comprising a split toxin sequence flanked by an intein fragment, wherein the intein fragment comprises an intein C-fragment, and wherein the split toxin sequence is C-terminal to an intein C-fragment; or c) an engineered antibody comprising a first Fc region comprising a first split toxin sequence flanked by a first intein fragment, wherein the first intein fragment comprises an intein N-fragment, wherein the first split toxin sequence is N-terminal to the intein N-fragment and a second Fc region comprising a second split toxin sequence flanked by a second intein fragment, wherein the second intein fragment comprises an intein C-fragment, wherein the second split toxin sequence is C-terminal to the intein C-fragment.

Disclosed herein are engineered platelets comprising: a) an engineered antibody comprising an Fc region that comprises a split toxin sequence flanked by an intein fragment, wherein the intein fragment comprises an intein N-fragment, and wherein the split toxin sequence is N-terminal to an intein N-fragment; b) an engineered antibody comprising an Fc region comprising a split toxin sequence flanked by an intein fragment, wherein the intein fragment comprises an intein C-fragment, and wherein the split toxin sequence is C-terminal to an intein C-fragment; or c) an engineered antibody comprising a first Fc region comprising a first split toxin sequence flanked by a first intein fragment, wherein the first intein fragment comprises an intein N-fragment, wherein the first split toxin sequence is N-terminal to the intein N-fragment and a second Fc region comprising a second split toxin sequence flanked by a second intein fragment, wherein the second intein fragment comprises an intein C-fragment, wherein the second split toxin sequence is C-terminal to the intein C-fragment.

Disclosed herein are populations of engineered platelets comprising: a) a first subpopulation of engineered platelets comprising an engineered antibody, comprising an Fc region comprising a split toxin sequence flanked by an intein fragment, wherein the intein fragment comprises an intein N-fragment, and wherein the split toxin sequence is N-terminal to an intein N-fragment; and b) a second subpopulation of engineered platelets comprising an engineered antibody, comprising an Fc region comprising a split toxin sequence flanked by an intein fragment, wherein the intein fragment comprises an intein C-fragment, and wherein the split toxin sequence is C-terminal to an intein C-fragment.

Disclosed herein are engineered antibodies, wherein the engineered antibodies comprises a first Fc region and a second Fc region: a) wherein the first Fc region comprises a split toxin sequence flanked by an intein fragment, wherein the intein fragment comprises an intein N-fragment, and wherein the split toxin sequence is N-terminal to an intein N-fragment; and b) wherein the second Fc region comprises a split toxin sequence flanked by an intein fragment, wherein the intein fragment comprises an intein C-fragment, and wherein the split toxin sequence is C-terminal to an intein C-fragment.

Disclosed herein are engineered antibodies, wherein the engineered antibodies comprise an Fc region, wherein the Fc region comprises: a) a split toxin sequence flanked by an intein fragment, wherein the intein fragment comprises an intein N-fragment, and wherein the split toxin sequence is N-terminal to an intein N-fragment; or b) a split toxin sequence flanked by an intein fragment, wherein the intein fragment comprises an intein C-fragment, and wherein the split toxin sequence is C-terminal to an intein C-fragment.

BRIEF DESCRIPTION OF THE DRAWINGS

FIG. 1A shows cellular distortion, inactivation and destruction in lysosomal storage diseases (LSD). FIG. 1B shows that megakaryocytes form platelets from their cytoplasmic extensions and that these formed platelets are filled with bioactive proteins. FIG. 1C shows engineered platelets filled with lysosomal enzymes. FIG. 1D shows non-engineered platelets are activated by thrombin and other small molecules. FIG. 1E shows that engineering designer receptors exclusively activated by designer drugs (DREADDs) on platelets so the receptor binds to pharmaceutically inert small molecules and no longer to the endogenous molecules.

FIG. 3A shows (i) cells isolated from mouse bone marrow, (ii) grown in Dexter culture for the specified days, (iii) cells were transferred to MethoCult, and (iv) the number of lineage-committed colonies were counted over time. FIG. 3B shows cells isolated from mouse bone marrow were (i) grown in MethoCult for 7 days and (ii) labeled with CD41 and CD45 to assess their differentiation. CD41 labels platelets (cells in P4 gate, pink), CD45 labels all nucleated cells of blood lineage (cells in the P3 gate, blue). Those cells labeled with both (cells in P2 gate, green) are MKs and progenitor cells. FIG. 3C shows LSK+ cells (HSCs) from the bone marrow were sorted and grown on OP9 stromal cells for 8 days. FIG. 3D shows ES cells were grown on OP9 stromal cells for 9 days, and LSK+ cells were detected by flow cytometry (cells in P3 gate, blue).

FIG. 4A shows that 3x attP sites that were inserted into the Rosa26 allele in mouse ES cells using CRISPR technology. FIG. 4B shows that using PhiC31 integrase, the genetic circuits can target the Rosa26 allele for stable integration. FIG. 4C shows the results of PCR screen to confirm integration. FIG. 4D shows the PCR results of cDNA from mouse using screening primers. Lane 1: 2-log ladder, lane2: wild type with no integration, land 3: insertion of landing pad.

FIG. 5A shows that metastasis occurs when circulating tumor cells (CTCs) detach from a primary tumor and enter the bloodstream to invade other tissues. CTCs survive in the bloodstream with the help of platelets, which surround the CTCs. The CTCs can activate the platelets and they secrete their protein contents. FIG. 5B shows that platelets can be made from megakaryocytes (MKs) to make the bioactive proteins to be packaged in the platelets. FIG. 5C shows engineered MKs can be filled with bioactive therapeutics using genetic tools to target and kill CTCs before they leave the bloodstream.

FIG. 6A shows intein-mediated restoration of the split toxic protein, α-sarcin. FIG. 6B is a schematic illustration of engineered monoclonal antibodies with split toxin proteins. Steps 1: Engineered monoclonal antibody recognizes CTC specific antigen, 2: The engineered monoclonal antibody is engulfed by the cell and enters the endosome/lysosome pathways where the engineered monoclonal antibody is processed and/or degraded, 3. The split toxin proteins (as illustrated a split α-sarcin protein) enter the cytoplasm, 4. The inteins spontaneously reassemble the split toxin protein, making it functional. 5. The highly toxic α-sarcin protein induces cell death.

FIG. 7A shows that the Lad repressor proteins are constitutively expressed (purple) and bind to the lac operator sites upstream of QF (orange) and GFP (green). FIG. 7B shows that when IPTG is present, it binds to the Lad proteins and produces a conformational change in the repressor proteins. FIGS. 8A-F show that LacQ controls gene expression in ES cells. FIG. 8A shows the bright field image and FIG. 8B shows the fluorescent image of stably transfected ES cells in the absence of IPTG. FIG. 8C shows bright field image and FIG. 8D shows the fluorescent image of stably transfected ES cells in the presence of 100 µM IPTG after 24 hours. FIG. 8E shows that LacQ is capable of tuning the level of gene expression in ES cells by adding different amounts of IPTG. GFP was quantified using flow cytometry 24 hours (light blue) and 48 hours (dark blue) after adding IPTG to the growth medium. FIG. 8F shows that the switching dynamics of LacQ-GFP were studied using flow cytometry by adding 100 µM IPTG for two days, and then removing IPTG from the medium. Each data point represents the mean of GFP expression in three independent experiments, and the error bars represent the standard deviation between these experiments.

FIG. 9A shows that platelets can be made from iPS cells by over expressing 3 genes (c-MYC, BMI1, and BCL-XL) to expand MKs, and when their expression is turned off, mature MKs can produce platelets in the presence of turbulent flow. FIG. 9B shows that in the absence of Cre, the 3 genes remain on and the gene for loading is off. Upon exposure to Cre recombinase, the DNA undergoes homologous recombination, cutting out the 3 genes and turning on the expression of the gene for the protein to be loaded into platelets.

DETAILED DESCRIPTION

Figure 1A:
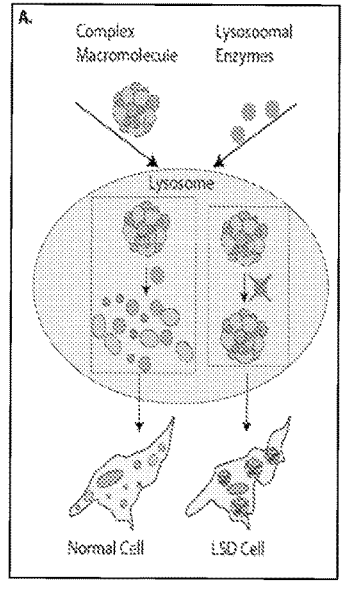
FIGS. 1A-E show engineered platelets as delivery systems for disease treatments.
Figure 1B:
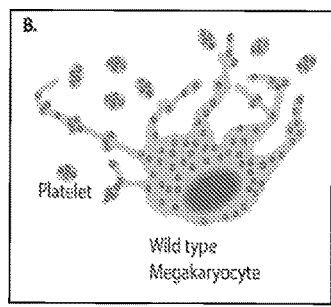
Figure 1C:
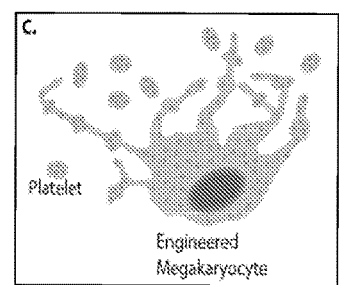
Figure 1D:
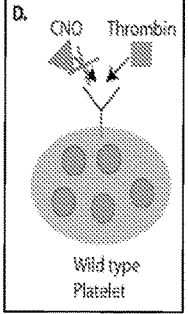
Figure 1E:
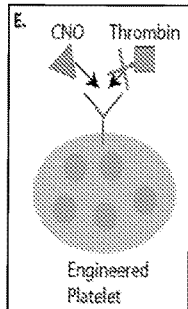

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "comprising" can include the aspects "consisting of" and "consisting essentially of."

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

The term "expression vector" is herein to refer to vectors that are capable of directing the expression of genes to which they are operatively-linked. Common expression vectors of utility in recombinant DNA techniques are often in the form of plasmids. Recombinant expression vectors can comprise a nucleic acid as disclosed herein in a form suitable for expression of the acid in a host cell. In other words, the recombinant expression vectors can include one or more regulatory elements or promoters, which can be selected based on the host cells used for expression that is operatively linked to the nucleic acid sequence to be expressed.

The term "sequence of interest" or "gene of interest" can mean a nucleic acid sequence (e.g., a therapeutic gene), that is partly or entirely heterologous, i.e., foreign, to a cell into which it is introduced.

The term "sequence of interest" or "gene of interest" can also mean a nucleic acid sequence, that is partly or entirely homologous to an endogenous gene of the cell into which it is introduced, but which is designed to be inserted into the genome of the cell in such a way as to alter the genome (e.g., it is inserted at a location which differs from that of the natural gene or its insertion results in "a knockout"). For example, a sequence of interest can be cDNA, DNA, or mRNA.

The term "sequence of interest" or "gene of interest" can also mean a nucleic acid sequence that is partly or entirely complementary to an endogenous gene of the cell into which it is introduced.

A "sequence of interest" or "gene of interest" can also include one or more transcriptional regulatory sequences and any other nucleic acid, such as introns, that may be necessary for optimal expression of a selected nucleic acid. A "protein of interest" means a peptide or polypeptide sequence (e.g., a therapeutic protein), that is expressed from a sequence of interest or gene of interest.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in some aspects, the inhibition or reduction can be a 10, 20, 30, 40, 50, 60, 70, 80, 90, 100%, or any amount of reduction in between as compared to native or control levels. In some aspects, the inhibition or reduction is 10-20, 20-30, 30-40, 40-50, 50-60, 60-70, 70-80, 80-90, or 90-100% as compared to native or control levels. In some aspects, the inhibition or reduction is 0-25, 25-50, 50-75, or 75-100% as compared to native or control levels.

"Modulate", "modulating" and "modulation" as used herein mean a change in activity or function or number. The change may be an increase or a decrease, an enhancement or an inhibition of the activity, function or number.

The terms "alter" or "modulate" can be used interchangeable herein referring, for example, to the expression of a nucleotide sequence in a cell means that the level of expression of the nucleotide sequence in a cell after applying a method as described herein is different from its expression in the cell before applying the method.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in some aspects, the increase or promotion can be a 10, 20, 30, 40, 50, 60, 70, 80, 90, 100%, or more, or any amount of promotion in between as compared to native or control levels. In some aspects, the increase or promotion is 10-20, 20-30, 30-40, 40-50, 50-60, 60-70, 70-80, 80-90, or 90-100% as compared to native or control levels. In some aspects, the increase or promotion is 0-25, 25-50, 50-75, or 75-100%, or more, such as 200, 300, 500, or 1000% more as compared to native or control levels. In some aspects, the increase or promotion can be greater than 100 percent as compared to native or control levels, such as 100, 150, 200, 250, 300, 350, 400, 450, 500% or more as compared to the native or control levels.

As used herein, "CRISPR system" and "CRISPR-Cas system" refers to transcripts and other elements involved in the expression of or directing the activity of CRISPR-associated ("Cas") genes, including sequences encoding a Cas gene, a guide sequence (also referred to as a "spacer" in the context of an endogenous CRISPR system; e.g. guide RNA or gRNA), or other sequences and transcripts from a CRISPR locus. In some aspects, one or more elements of a CRISPR system is derived from a type I, type II, or type III CRISPR system. In some aspects, one or more elements of a CRISPR system are derived from a particular organism comprising an endogenous CRISPR system, such as *Strep-*

*tococcus pyogenes*. Generally, a CRISPR system is characterized by elements that promote the formation of a CRISPR complex at the site of a target sequence (also referred to as a proto spacer in the context of an endogenous CRISPR system).

As used herein, the terms "disease" or "disorder" or "condition" are used interchangeably referring to any alternation in state of the body or of some of the organs, interrupting or disturbing the performance of the functions and/or causing symptoms such as discomfort, dysfunction, distress, or even death to the person afflicted or those in contact with a person. A disease or disorder or condition can also related to a distemper, ailing, ailment, malady, disorder, sickness, illness, complaint, or affection.

As used herein, the terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription.

Suitable promoters can be derived from genes of the host cells where expression should occur or from pathogens for this host cells (e.g., tissue promoters or pathogens like viruses). If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots or meristem. The term "tissue specific" as it applies to a promoter refers to a promoter that is capable of directing selective expression of a nucleotide sequence or gene of interest to a specific type of tissue in the relative absence of expression of the same nucleotide sequence or gene of interest in a different type of tissue.

Although the foregoing invention has been described in some detail by way of illustration and example for purposes of clarity of understanding, certain changes and modifications may be practiced within the scope of the appended claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

More than 90% of cancer-associated deaths are caused by metastasis[8]. For this reason, an important goal in cancer research is limiting metastasis, which occurs when some cancer cells, also called circulating tumor cells (CTCs), detach from primary tumor sites and enter the bloodstream to invade other tissues and organs at different locations. Once CTCs enter into the bloodstream, they face many survival challenges including immunological attack, shear forces, and apoptosis. To enhance their survival rate, CTCs strongly attract platelets to form a protective cloak that helps the cancer cells survive the forces in the bloodstream and to escape immune surveillance (Erpenbeck L, Schon M P. *Blood* 2010; 115(17): 3427-36; Labelle M, Hynes R O.

Cancer Discov 2012; 2(12): 1091-9; Stegner D, et al. Thrombosis research 2014; 133 Suppl 2: S149-57; Lou X L, et al. Chin J Cancer Res 2015; 27(5): 450-60; Gay L J, Felding-Habermann B. Nat Rev Cancer 2011; 11(2): 123-34; Li N. Int J Cancer 2016; 138(9): 2078-87; Borsig L. Expert Rev Anticancer Ther 2008; 8(8): 1247-55; Honn K V, et al. Cancer Metastasis Rev 1992; 11(3-4): 325-51; Ward Y, et al. Cell Rep 2018; 23(3): 808-22; and Yu L X, et al. Nature communications 2014; 5: 5256). Although the mechanisms by which platelets interact with circulating tumor cells are poorly understood, studies have shown that they are involved in cancer progress, especially during metastasis where platelets help to degrade extracellular matrix (ECM) to support the colonization of cancer cells in distant locations from the original tumor formation site (Gay U, Felding-Habermann B. Nat Rev Cancer 2011; 11(2): 123-34; Li N. Int J Cancer 2016; 138(9): 2078-87; Borsig L. Expert Rev Anticancer Ther 2008; 8(8): 1247-55; and Honn K V, et al. Cancer Metastasis Rev 1992; 11(3-4): 325-51).

Figure 2:
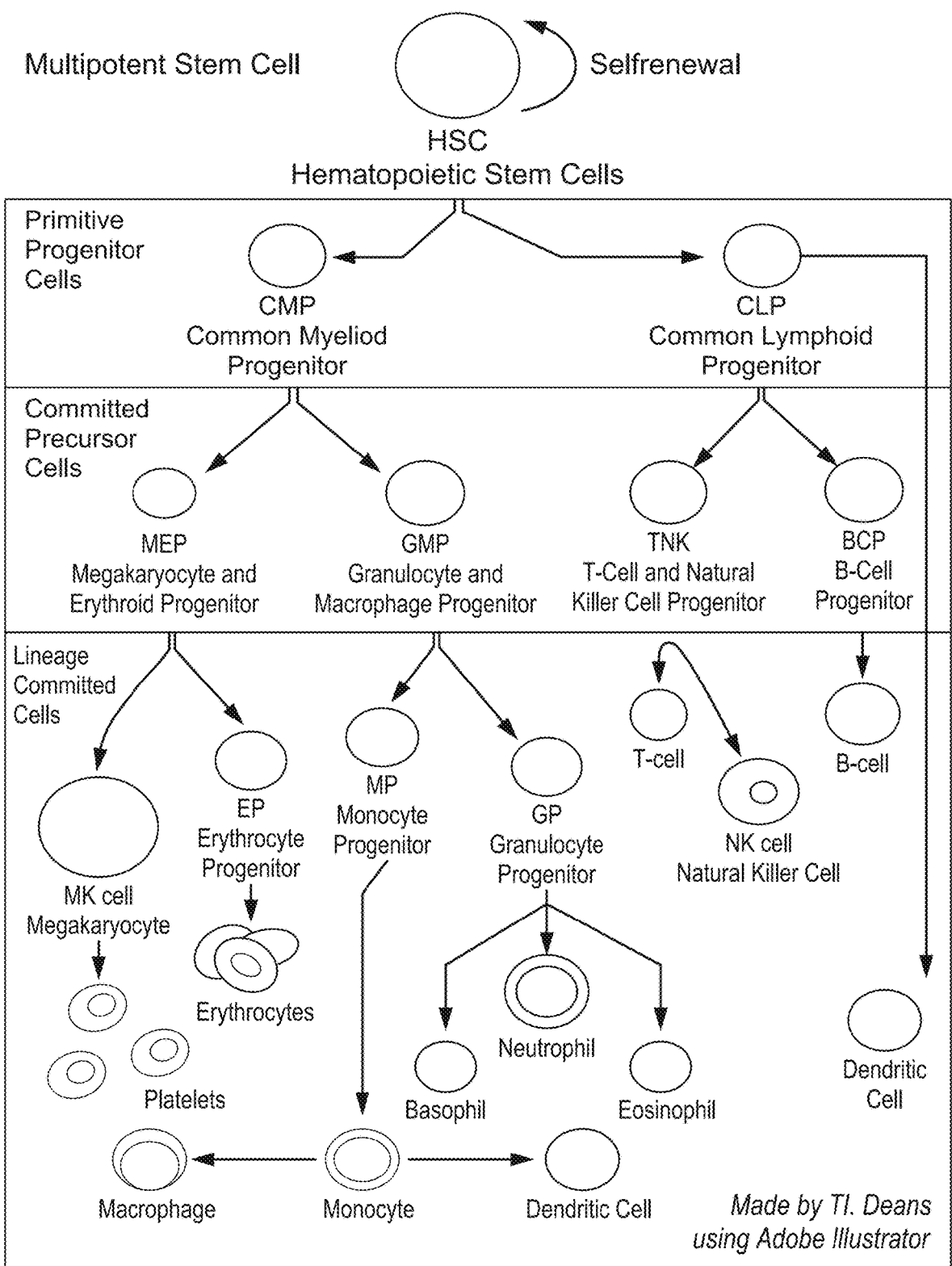
FIG. 2 shows an overview of HSC differentiation. HSCs are multipotent stem cells that have the potential to differentiate into various precursor cells that become more specialized blood cells.

In the bone marrow, platelets are derived from the process of hematopoiesis, the differentiation of hematopoietic stem cells (HSCs) into specialized blood and immune cells (FIG. 2) (Chang Y, et al. Journal of thrombosis and haemostasis: JTH 2007; 5 Suppl 1: 318-27) and play an important role in homeostasis, wound healing, angiogenesis, inflammation, and clot formation (Chang Y, et al. Journal of thrombosis and haemostasis: JTH 2007; 5 Suppl 1: 318-27; Kuter D J. Seminars in hematology 2010; 47(3): 243-8; Morrison S J, Uchida N, Weissman I L. Annual review of cell and developmental biology 1995; 11: 35-71; and Mosaad Y M. Transfusion and apheresis science: official journal of the World Apheresis Association: official journal of the European Society for Haemapheresis 2014; 51(3): 68-82). Platelets circulate in large numbers throughout the body with an average lifespan of 9-10 days. The source of this large cell population is from their progenitor cells, megakaryocytes (MK). In general, platelets are in a resting, inactive, state and require a trigger before becoming activated. Upon activation, platelets secrete more than 300 active biomolecules from their intracellular granules. Therefore, platelets possess many unique characteristics that make them attractive candidates for targeting CTCs and for the in vivo delivery of natural and synthetic payloads: 1) they naturally associate with circulating tumor cells, 2) they have extensive circulation range in the body, 3) they are anucleate cells, 4) they are biocompatible, 5) their average lifespan in humans is ~10 days, and 6) following activation, their protein granules serve as secretory vesicles, releasing components into the extracellular fluid. The compositions and methods disclosed herein take advantage of platelets' innate association with circulating tumor cells and their storage, trafficking, and release capacities of small molecules, to engineer them as delivery vehicles for the development of next generation delivery methods for targeting and destroying CTCs to prevent or minimize metastasis. Also disclosed herein is the development of genetic circuits that can be used to direct pluriopotent cell differentiation to produce platelets loaded with engineered antibodies in vitro, and computational modeling and computer simulations to develop genetic tools for platelets to control when and where the engineered platelets release their therapeutic payload (e.g., engineered antibodies, split inteins or split toxins), thus reprogramming the spatial and temporal activity of platelets.

Inteins are protein elements that reassemble proteins covalently from two precursor fragments in a process known as protein splicing that occurs spontaneously and requires no exogenous energy or co-factors (Perler F B. IUBMB Life 2005; 57(7): 469-76; Wong S, et al. Protein Eng Des Sel 2013; 26(3): 207-13; and Nogami S, Satow Y, Ohya Y, Anraku Y. Probing novel elements for protein splicing in the yeast Vmal protozyme: a study of replacement mutagenesis and intragenic suppression. Genetics 1997; 147(1): 73-85). Intein technology has been exploited in may applications where conditional protein splicing of the S. cerevisiae Sce-VMA intein can be artificially split, rendering the separate halves inactive such they require a condition for co-localization and assembly (Mootz H D, Muir T W. Journal of the American Chemical Society 2002; 124(31): 9044-5). The repertoire of trans-splice-inducing conditions has expanded and now includes temperature, light and protein-scaffold activation (Schwartz E C, et al. Nature chemical biology 2007; 3(1): 50-4; Selgrade D F, et al. Journal of the American Chemical Society 2013; 135(20): 7713-9; Tyszkiewicz A B, Muir T W. Nature methods 2008; 5(4): 303-5; and Zeidler M P, et al. Temperature-sensitive control of protein activity by conditionally splicing inteins. Nature biotechnology 2004; 22(7): 871-6. As described herein, this technology can be used to split a toxin into to two corresponding split toxin sequences, for example α-sarcin, a ribosome inactivating protein that kills cells in its assembled active form (FIG. 6), is a toxin that can be split into corresponding inactive split toxin sequences. Each inactive split toxin can be produced separately and loaded into separate platelet populations that will target different receptors on CTCs. Once each inactive split toxin is in the CTC, they can spontaneously assemble and kill the CTC.

Disclosed herein are engineered platelets that are designed to target and destroy circulating tumor cells. Cells are complex and dynamic systems that have the remarkable ability to continuously sense, integrate, store, and respond to these signals throughout their lives, making cell therapy an attractive avenue for next-generation cancer treatments. Platelets are attractive in cancer therapeutic settings for targeting CTCs because they associate with CTCs, and many studies have shown that CTCs express a wide variety of receptors for attracting platelets to bind and, upon binding, promote their activation and release of their cellular contents (Lou X L, et al. Chin J Cancer Res 2015; 27(5): 450-60; and Yu L X, et al. Nature communications 2014; 5: 5256). Synthetic biology has transformed how cells can be reprogrammed, providing a means to reliably and predictably control cell behavior with the assembly of genetic parts into more complex gene circuits (Weisenberger M S, Deans T L. J Ind Microbiol Biotechnol 2018; 45(7): 599-614). Megakaryocytes, the progenitor cells of platelets, are amenable to high-level reprogramming through synthetic biology. Described herein are methods to engineer blood platelets to be filled with inactive split toxins fused to monoclonal antibodies that specifically bind to CTC receptors. Once each half of the split toxin can be internalized by the CTC, the parts will spontaneously assemble to create a functional toxic protein and kill the CTC.

Compositions

Genetic circuits/nucleic acid constructs. Disclosed herein are nucleic acid constructs comprising one or more promoters operatively linked to: i) a first recombination site; ii) c-MYC, BMI1, and BCL-XL genes; and iii) a second recombination site; and b) a sequence capable of encoding an engineered antibody sequence, wherein the engineered antibody sequence comprises a split toxin sequence flanked by an intein sequence, and wherein the sequence capable of encoding the engineered antibody sequence is out of frame from the promoter. In some aspects, the one or more promoters can be regulatable. In some aspects, the one or more promoters can be regulated by one or more media modulators. In some aspects, the media modulators can be used to direct differentiation of a stem cell to a specific cell type. In some aspects, the one or more media modulators can facilitate the differentiation of a pluripotent stem cell to a megakaryocyte. In some aspects, the one or more media modulators can facilitate the differentiation of a megakaryocyte to a platelet. In some aspects, the one or more media modulators can facilitate the differentiation of a pluripotent stem cell to a platelet. In some aspects, the one or more media modulators can be isopropyl β-D-1-thiogalactopyranoside (IPTG), tetracycline, doxycycline, quinic acid, or auxin. In some aspects, the one or more media modulators can activate the one or more promoters. In some aspects, the one or more promoters can be constitutively active. In some aspects, the one or more promoters can be CMV, RSV, U6, beta actin, or elongation factor promoter. In some aspects, the first or second recombination sites can be loxP, attP, Bxb1 or a combination thereof. In some aspects, c-MYC, BMI1, and BCL-XL genes can be flanked by the first recombination site and the second recombination site. In some aspects, the expression of the engineered antibody sequence can be repressed. In some aspects, the expression of the engineered antibody can be induced in the presence of one or more recombinases that cleave the recombinase sites. In some aspects, the one or more recombinases can be Cre, phiC31 or Bxb1. In some aspects, the one or more recombinases can cleave the recombinase sites and bring the engineered antibody sequence in frame with the promoter. In some aspects, the engineered antibody sequence can comprise a split toxin sequence flanked by a first intein fragment, wherein the intein fragment comprises an intein N-fragment, wherein the split toxin sequence is N-terminal to an intein N-fragment. In some aspects, the engineered antibody sequence can comprise a split toxin sequence flanked by an intein fragment, wherein the intein fragment comprises an intein C-fragment, wherein the split toxin sequence is C-terminal to an intein C-fragment.

Split toxins. As used herein the term "split toxin" or "split toxin sequence" can be used to mean a portion or a fragment of an active toxin sequence. Two portions or fragments of an active toxin sequence, when fused or ligated to another portion or fragment of the active toxin sequence can form an active toxin complex or an active toxin sequence. Toxin splicing using a split intein system can use artificial fragmentation of an active toxin sequence and tethering each portion or fragment of the active toxin sequence to a split intein fragment to form a chimeric toxin-intein fusion. The portion or a fragment of an active toxin sequence of the chimeric toxin-intein fusion can be reconstituted into an active toxin, such that the split toxin sequences of the chimeric toxin-intein fusions are recombined upon degradation after uptake into a target cell (e.g., circulating tumor cell). These chimeric toxin-intein fusions remain nontoxic until degradation, resulting in activation of intein splicing and fusion or ligation of the portions or fragments of the toxin sequence to form an active toxin sequence or active toxin complex. Considerations for the engineering and implementation of toxin splicing systems include: choice of toxin split site, split site (extein) chemistry, and temperature sensitivity.

The term "complementary split toxin sequences" or "complementary split toxins" is used herein refer to two portions or two fragments of an active toxin sequence, that when fused or ligated to each other can form an active toxin complex or an active toxin sequence. Complementary split toxins can refer to an N-split toxin and a C-split toxin portion or a fragment (e.g., the split toxin C-fragment (C-terminal fragment) or the split toxin N-fragment (N-terminal fragment).

Toxin splicing using a split intein system can use artificial fragmentation of an active toxin sequence to form a split toxin sequence. The split toxin sequence can be tethered and to a split intein fragment to form a chimeric toxin-intein fusion (e.g., a split toxin sequence flanked by an intein sequence). The split toxin sequence of a chimeric toxin-intein fusion can be reconstituted into an active toxin, such that the split toxin sequences of the chimeric toxin-intein fusions are recombined upon degradation after uptake into a target cell (e.g., circulating tumor cell). A chimeric toxin-intein fusion can remain nontoxic until degradation, resulting in activation of intein splicing and fusion or ligation of the complementary split toxin sequence to form an active toxin sequence or active toxin complex. Considerations for the engineering and implementation of toxin splicing systems include: choice of toxin split site, split site (extein) chemistry, and temperature sensitivity.

Figures 6A, 6B:
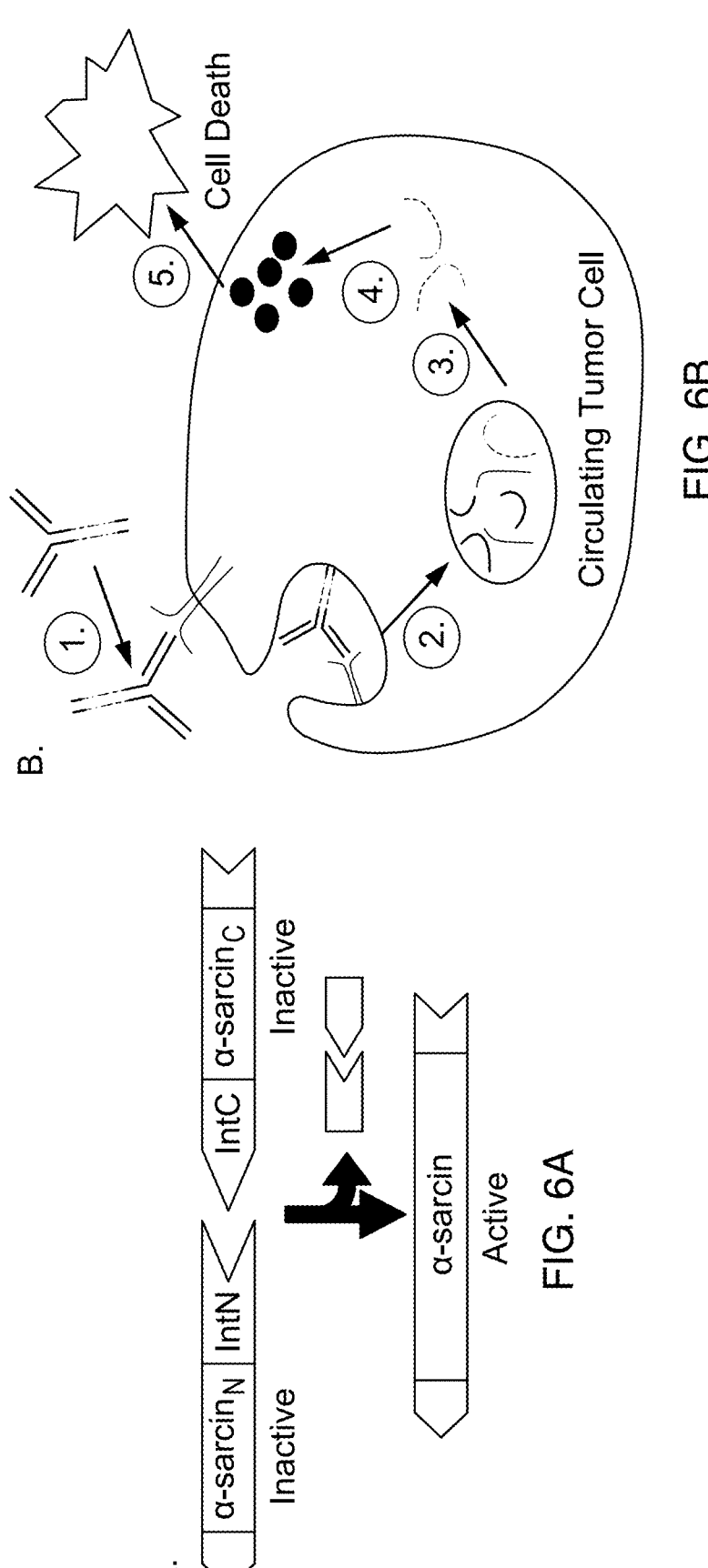
FIGS. 6A-B showed targeted CTC killing.

In some aspects, a toxin such as alpha-sarcin can be split into an N-terminal fragment (e.g., a split toxin N-fragment) and a C-terminal fragment (e.g., a split toxin C-fragment). In some aspects, the alpha-sarcin can be split into an N-terminal β-hairpin fragment and a C-terminal catalytic fragment based on its structure. Referring to FIG. 6B, once the engineered antibody is engulfed by the circulating tumor cell and enters the endosome/lysosome pathways and is degraded, the split toxin sequence flanked by an intein fragment, wherein the intein fragment comprises an intein C-fragment, wherein the split toxin sequence is C-terminal to an intein C-fragment; and the split toxin sequence flanked by an intein fragment, wherein the intein fragment comprises an intein N-fragment enter the cytoplasm, and binding of the intein fragment comprising the intein N-fragment to the intein fragment comprising the intein C-fragment forming an intein complex, wherein the intein complex is inactive, and binding of the split toxin sequence that is N-terminal to the intein N-fragment to the split toxin sequence that is C-terminal to the intein C-fragment forming a toxin complex, wherein the toxin complex is active. The intein is reconstituted, and the split toxin is spliced to induce apoptosis. The individual fragment constructs of the split toxin are not toxic when expressed independently (e.g., split toxin sequences). After degradation in the circulating tumor cell, the intein fragments reconstitute and splice N- and C-split toxin sequences together, forming a functional toxin (e.g., alpha-sarcin).

Nucleic acid sequences encoding active toxins and their respective split toxins and their corresponding amino acid sequences are known.

Pluripotent stem cells. Disclosed herein are pluripotent stem cells. Disclosed herein are pluripotent stem cells comprising any of the nucleic acid constructs disclosed herein. Disclosed herein are pluripotent stem cells comprising any of the genetic circuits disclosed herein. In some aspects, the pluripotent stem cell can be a hematopoietic progenitor stem cell, an embryonic stem cell or an induced pluripotent stem cell (iPSC). In some aspects, the pluripotent stem cells are derived from cord blood or bone marrow. In some aspects, the iPSC can be derived from blood cells. In some aspects, the pluripotent stem cells can be human pluripotent stem cells.

Megakaryocytes. Disclosed herein are megakaryocytes. Disclosed herein are megakaryocytes at any development stage. Disclosed herein are megakaryocytes comprising any of the nucleic acid constructs described herein. Disclosed herein are megakaryocytes comprising a nucleic acid construct. In some aspects, the nucleic acid constructs can comprise one or more promoters operatively linked to: i) a first recombination site; ii) a second recombination site; and iii) a sequence capable of encoding an engineered antibody sequence, wherein the engineered antibody sequence comprises a split toxin sequence flanked by an intein sequence, wherein the sequence capable of encoding the engineered antibody sequence is in frame with the promoter. Disclosed herein are engineered antibody sequences comprising: a) a split toxin sequence flanked by a first intein fragment, wherein the split toxin fragment is N-terminal to an intein N-fragment; b) a split toxin sequence flanked by an intein fragment, wherein the split toxin fragment is C-terminal to an intein C-fragment; or c) a combination thereof.

Also disclosed herein are engineered megakaryocytes comprising engineered antibodies. In some aspects, the engineered megakaryocytes can comprise: a) an engineered antibody comprising an Fc region comprising a split toxin sequence flanked by an intein fragment, wherein the intein fragment comprises an intein N-fragment, and wherein the split toxin sequence is N-terminal to an intein N-fragment; b) an engineered antibody comprising an Fc region comprising a split toxin sequence flanked by an intein fragment, wherein the intein fragment comprises an intein C-fragment, and wherein the split toxin sequence is C-terminal to an intein C-fragment; or c) an engineered antibody comprising a first Fc region comprising a first split toxin sequence flanked by a first intein fragment, wherein the first intein fragment comprises an intein N-fragment, wherein the first split toxin sequence is N-terminal to the intein N-fragment and a second Fc region comprising a second split toxin sequence flanked by a second intein fragment, wherein the second intein fragment comprises an intein C-fragment, wherein the second split toxin sequence is C-terminal to the intein C-fragment. In some aspects, the split toxin sequence that is N-terminal to the intein N-fragment and the split toxin sequence that is C-terminal to the intein C-fragment or the first and the second split toxin sequences are consecutive fragments of the same toxin. In some aspects, the split toxin sequence that is N-terminal to the intein N-fragment and the split toxin sequence that is C-terminal to the intein C-fragment or the first and the second split toxin sequences are fragments of α-sarcin. In some aspects, the intein C-fragment and the intein N-fragment or the first and second intein fragments are fragments of *S. cerevisiae* SceVMA intein. In some aspects, the Fc region or the first Fc region and the second Fc region are Fc regions of an IgG antibody or fragment thereof. In some aspects, the IgG antibody or fragment thereof can comprise a tumor-associated antigen recognition site. In some aspects, the IgG antibody or fragment thereof can be an anti-Her-2 antibody.

Platelets. Disclosed herein are platelets. Disclosed herein are engineered platelets. Disclosed herein are engineered platelets comprising engineered antibodies. In some aspects, the engineered platelets can comprise: a) an engineered antibody comprising an Fc region that comprises a split toxin sequence flanked by an intein fragment, wherein the intein fragment comprises an intein N-fragment, and wherein the split toxin sequence is N-terminal to an intein N-fragment; b) an engineered antibody comprising an Fc region comprising a split toxin sequence flanked by an intein fragment, wherein the intein fragment comprises an intein C-fragment, and wherein the split toxin sequence is C-terminal to an intein C-fragment; or c) an engineered antibody comprising a first Fc region comprising a first split toxin sequence flanked by a first intein fragment, wherein the first intein fragment comprises an intein N-fragment, wherein the first split toxin sequence is N-terminal to the intein N-fragment and a second Fc region comprising a second split toxin sequence flanked by a second intein fragment, wherein the second intein fragment comprises an intein C-fragment, wherein the second split toxin sequence is C-terminal to the intein C-fragment. In some aspects, the split toxin sequence that is N-terminal to the intein N-fragment and the split toxin sequence that is C-terminal to the intein C-fragment or the first and the second split toxin sequences are consecutive fragments of the same toxin. In some aspects, the split toxin sequence that is N-terminal to the intein N-fragment and the split toxin sequence that is C-terminal to the intein C-fragment or the first and the second split toxin sequences are fragments of α-sarcin. In some aspects, the intein C-fragment and the intein N-fragment or the first and second intein fragments are fragments of *S. cerevisiae* SceVMA intein. In some aspects, the Fc region or the first Fc region and the second Fc region are Fc regions of an IgG antibody or fragment thereof. In some aspects, the IgG antibody or fragment thereof comprises a tumor-associated antigen recognition site. In some aspects, the IgG antibody or fragment thereof can be an anti-Her-2 antibody.

Also disclosed herein are populations of engineered platelets. In some aspects, the population of engineered platelets can comprise a) a first subpopulation of engineered platelets comprising an engineered antibody, comprising an Fc region comprising a split toxin sequence flanked by an intein fragment, wherein the intein fragment comprises an intein N-fragment, and wherein the split toxin sequence is N-terminal to an intein N-fragment; and b) a second subpopulation of engineered platelets comprising an engineered antibody, comprising an Fc region comprising a split toxin sequence flanked by an intein fragment, wherein the intein fragment comprises an intein C-fragment, and wherein the split toxin sequence is C-terminal to an intein C-fragment. In some aspects, the split toxin sequence that is N-terminal to the intein N-fragment and the split toxin sequence that is C-terminal to the intein C-fragment are fragments of a split toxin and when recombined form an active toxin. In some aspects, the split toxin sequence that is N-terminal to the intein N-fragment and the split toxin sequence that is C-terminal to the intein C-fragment are fragments of α-sarcin. In some aspects, the intein C-fragment and the intein N-fragment are fragments of *S. cerevisiae* SceVMA intein. In some aspects, the Fc region is the Fc region of an IgG antibody or fragment thereof. In some aspects, the IgG antibody or fragment thereof can comprise a tumor-associated antigen recognition site. In some aspects, the IgG antibody or fragment thereof can be an anti-Her-2 antibody.

Engineered antibodies. Disclosed herein are engineered antibodies. Disclosed herein are engineered antibodies comprising a first Fc region and a second Fc region: a) wherein the first Fc region comprises a split toxin sequence flanked by an intein fragment, wherein the intein fragment comprises an intein N-fragment, and wherein the split toxin sequence is N-terminal to an intein N-fragment; and b) wherein the second Fc region comprises a split toxin sequence flanked by an intein fragment, wherein the intein fragment comprises an intein C-fragment, and wherein the split toxin sequence is C-terminal to an intein C-fragment. In some aspects, the split toxin sequence that is N-terminal to the intein N-fragment and the split toxin sequence that is C-terminal to the intein C-fragment are fragments of a split toxin and when recombined form an active toxin. In some aspects, the split toxin sequence that is N-terminal to the intein N-fragment and the split toxin sequence that is C-terminal to the intein C-fragment are fragments of α-sarcin. In some aspects, the intein C-fragment and the intein N-fragment are fragments of *S. cerevisiae* SceVMA intein. In some aspects, the first Fc region and the second Fc region can be Fc regions of an IgG antibody or fragment thereof. In some aspects, the IgG antibody or fragment thereof can comprise a tumor-associated antigen recognition site. In some aspects, the IgG antibody or fragment thereof can be an anti-Her-2 antibody.

Disclosed herein are engineered antibodies, wherein the engineered antibody comprises an Fc region, wherein the Fc region comprises: a) a split toxin sequence flanked by an intein fragment, wherein the intein fragment comprises an intein N-fragment, and wherein the split toxin sequence is N-terminal to an intein N-fragment; or b) a split toxin sequence flanked by an intein fragment, wherein the intein fragment comprises an intein C-fragment, and wherein the split toxin sequence is C-terminal to an intein C-fragment. In some aspects, the split toxin sequence that is N-terminal to the intein N-fragment and the split toxin sequence that is C-terminal to the intein C-fragment are fragments of a split toxin and when recombined form an active toxin. In some aspects, the split toxin sequence that is N-terminal to the intein N-fragment and the split toxin sequence that is C-terminal to the intein C-fragment are fragments of α-sarcin. In some aspects, the intein C-fragment and the intein N-fragment are fragments of *S. cerevisiae* SceVMA intein. In some aspects, the Fc region can be the Fc region of an IgG antibody or fragment thereof. In some aspects, the IgG antibody or fragment thereof can comprise a tumor-associated antigen recognition site. In some aspects, the IgG antibody or fragment thereof can be an anti-Her-2 antibody.

Methods of Producing Platelets or Populations of Platelets

Disclosed herein are method of producing platelets or a population of platelets. Disclosed herein are methods of producing platelets or a population of platelets comprising an engineered antibody. In some aspects, the methods can comprise: a) providing pluripotent stem cells comprising any of the nucleic acid constructs of disclosed herein; b) culturing the pluripotent stem cells in a media under conditions to permit the expansion of the pluripotent stem cells to megakaryocytes; c) exposing the megakaryocytes to a recombinase under conditions suitable to catalyze a site specific recombination event between the first recombination site and the second recombination site, thereby excising c-MYC, BMI1, and BCL-XL, and bringing the sequence capable of encoding the engineered antibody sequence in frame with the promoter, and d) differentiating the megakaryocytes into platelets; wherein the platelets comprise the engineered antibody encoded by the engineered antibody sequence. In some aspects, the engineered antibody can comprise: a) an Fc region that comprises a split toxin sequence flanked by an intein fragment, wherein the intein fragment comprises an intein N-fragment, and wherein the split toxin sequence is N-terminal to an intein N-fragment; b) an Fc region comprising a split toxin sequence flanked by an intein fragment, wherein the intein fragment comprises an intein C-fragment, and wherein the split toxin sequence is C-terminal to an intein C-fragment; or c) a first Fc region comprising a first split toxin sequence flanked by a first intein fragment, wherein the first intein fragment comprises an intein N-fragment, wherein the first split toxin sequence is N-terminal to the intein N-fragment and a second Fc region comprising a second split toxin sequence flanked by a second intein fragment, wherein the second intein fragment comprises an intein C-fragment, wherein the second split toxin sequence is C-terminal to the intein C-fragment.

In some aspects, the media can comprise one or more media modulators. In some aspects, the media modulators can be used to direct differentiation of a stem cell to a specific cell type. In some aspects, the one or more media modulators can facilitate the differentiation of a pluripotent stem cell to a megakaryocyte. In some aspects, the one or more media modulators can facilitate the differentiation of a megakaryocyte to a platelet. In some aspects, the one or more media modulators can facilitate the differentiation of a pluripotent stem cell to a platelet. In some aspects, the one or more media modulators can be isopropyl β-D-1-thiogalactopyranoside (IPTG), tetracycline, doxycycline, quinic acid, or auxin. In some aspects, the one or more media modulators can be isopropyl β-D-1-thiogalactopyranoside (IPTG). In some aspects, the recombinase can be Cre. In some aspects, the pluripotent stem cell can be a hematopoietic progenitor stem cell, an embryonic stem cell or an induced pluripotent stem cell (iPSC). In some aspects, the pluripotent stem cell can be derived from cord blood or bone marrow. In some aspects, the iPSC can be derived from blood cells. In some aspects, the pluripotent stem cell can be a human pluripotent stem cell. In some aspects, the split toxin sequence that is N-terminal to the intein N-fragment and the split toxin sequence that is C-terminal to the intein C-fragment or the first split toxin sequence and the second split toxin are fragments of a split toxin and when recombined form an active toxin. In some aspects, the split toxin sequence that is N-terminal to the intein N-fragment and the split toxin sequence that is C-terminal to the intein C-fragment or the first split toxin sequence and the second split toxin sequence are fragments of α-sarcin. In some aspects, the intein C-fragment and the intein N-fragment are fragments of *S. cerevisiae* SceVMA intein or the first intein fragment and the second intein fragment are fragments of *S. cerevisiae* SceVMA intein. In some aspects, the Fc region or the first Fc region and the second Fc region are Fc regions of an IgG antibody or fragment thereof. In some aspects, the IgG antibody or fragment thereof can comprise a tumor-associated antigen recognition site. In some aspects, the IgG antibody or fragment thereof can be an anti-Her-2 antibody. In some aspects, the method can further comprise isolating or purifying the platelets.

Inteins. An intein used in any of the compositions and methods described herein can be isolated and cloned using methods known to one of ordinary skill in the art. Inteins useful in the disclosed nucleic acid constructs and methods disclosed herein are also commercially available. In some aspects, the intein can be engineered for N- and/or C-terminal cleavage unless the wild type intein displays the desired cleavage activities. In some aspects, a modified intein with the desired cleavage properties can be generated by substituting one or more residues within and/or flanking the intein sequence. For example, a modified intein having N-terminal cleavage activity can be created by changing the last intein residue. Alternatively, a modified intein with C-terminal cleavage activity can be created by changing the first intein residue.

In some aspects, the intein can be a split intein. The term "split intein", as used herein, refers to a protein, either isolated from nature or created through recombinant DNA technology, that has the following properties: (1) the protein occurs in two halves that interact with high affinity and selectivity; (2) the two halves must contain all intein sequences required for catalytic activity and may also contain appended non-intein peptidic sequences; (3) the protein has enzymatic activity only when the two halves are tightly associated; and (4) the enzymatic activity is site selective peptidic cleavage or ligation that serves to separate intein sequences from non-intein peptidic sequences or ligate the non-intein peptidic sequences into contiguous linear or circular proteins.

In some aspects, the intein can be a split intein, a naturally split intein DnaE from *Nostoc punctiforme*, and/or selected from the group consisting of Ssp from *Synechocystis* species, Aha from *Aphanothece halophytica*, Aov from *Aphanizomenon ovalisporum*, Asp from *Anabaena* species, Ava from *Anabaena variabilis*, Cra(CS505) from *Cylindrospermopsis raciborskii*, Csp (CCYOllO) from *Cyanotilece* species, Csp (PCC8801) from Cyanothece species, Cwa from Crocosphaera *watsonii*, Maer (NIES843) from *Microcystis aeruginosa*, Mcht (PCC7420)-2 from *Microcoleus chthonoplastes*, Oli from *Oscillatoria limnetica*, Sel (PC7942) from Synechococcus elongates, Ssp[PCC7002] from *Synechococcus* species, Tel from *Thernlosynechococcus elongates*, Ter-3 from *Trichodesmium erythraeum*, and Tvu from *Thernlosynechococcus vulcanus*. In some aspects, the intein is from *S. cerevisiae* SceVMA.

The term "complementary inteins" is used herein to refer to the N-intein and C-intein portions or fragments (e.g., the intein C-fragment or the intein N-fragment) of a split intein pair.

The term "N-intein" or "intein N-fragment", as used herein, refers to an intein polypeptide having homology to the N-terminal portion of a single intein polypeptide, and which associates with a complementary C-intein (or intein C-fragment) to form an active intein enzyme.

The term "C-intein" or "intein C-fragment", as used herein, refers to an intein polypeptide having homology to the C-terminal portion of a single intein polypeptide, and which associates with a complementary N-intein (or intein N-fragment) to form an active intein enzyme.

The term "extein", as used herein, refers to N- and C-terminal peptidic sequences that are fused to N- and C-inteins in nature and are manipulated (e.g., cleaved or ligated) through the enzymatic action of the split intein.

The term "peptidic", as used herein, refers to peptides and proteins longer than two amino acids in length that may also incorporate non-amino acid molecules (e.g., chromaphores, drugs, toxins, imaging contrast agents, etc.).

Inteins are a class of autocatalytic enzymes that contain both protease and ligase activities that function in the natural life cycle of these molecules. It has been demonstrated that intein reagents have utility for the cleavage, ligation, and circularization of peptidic substrates. In 1998, a new class of inteins termed "split inteins" was discovered where the enzyme occurs naturally in two parts, termed the N-intein (e.g., intein N-fragment) and C-intein (e.g., intein C-fragment) (complementary half inteins). While split inteins have been found in a broad variety of lower prokaryotes (Zettler J., et al, *FEBS Letters,* 553:909-914 (2009); Dassa B., et al, *Biochemistry,* 46:322-330 (2007); Choi J., et al, *J Mol Biol* 556: 1093-1106 (2006); Caspi, et al, *Mol Microbiol.,* 50: 1569-1577 (2003); Liu X. and Yang J., J *Biol Chem.,* 275:26315-26318 (2003); Wu H., et al, *Proc Natl Acad Sci USA.* 5:9226-9231 (1998)), no split inteins have been identified in eukaryotes. Two split inteins have been characterized that are both extremely fast and fairly promiscuous with respect to adjoining extein sequences. One class is the Npu DnaE intein (Iwai I., et al, *FEBS Letters* 550: 1853-1858 (2006); Zettler J., et al, *FEBS Letters,* 553:909-914 (2009)) and the other, the GP41 split inteins identified from meta-genomic data (Carvajal-Vallejos P., et al, *J. Biol. Chem.* 287: 28686-28696 (2012); International PCT Publication No. WO2013045632).

The N- and C-inteins (e.g., intein N- and C-fragments), with attached exteins (the two half proteins that will be joined by intein activity), associate extremely specifically and tightly through multiple inter-domain interactions to form the active intein enzyme (Shah N. H., et al, *J. Amer. Chem. Soc.* 135: 18673-18681; Dassa B., et al, *Nucl. Acids Res.,* 37:2560-2573 (2009)). In addition to the ligase and protease activities present in the first class of inteins, the split inteins have utility in affinity separations due to the tight and selective interaction of the N- and C-intein domains (e.g., intein N- and C-fragments).

Fusion proteins. The term "fusion protein" refers to a naturally occurring, synthetic, semi-synthetic or recombinant single protein molecule that comprises all or a portion of two or more polypeptides joined by peptide bonds. For example, complementary split toxin sequences such as an N-terminal fragment (e.g., a split toxin N-fragment) and a C-terminal fragment (e.g., a split toxin C-fragment) joined together can form a fusion protein.

Methods of preparing fusion, or chimeric, proteins are well known in the art including, but not limited to, standard recombinant DNA techniques. For example, DNA fragments coding for different protein sequences (e.g., an N-intein and a split toxin fragment; a C-intein and a split toxin fragment, wherein the split toxin fragments are complementary split toxins (or complementary exteins)) are ligated together in-frame in accordance with conventional techniques. In another embodiment, the fusion gene can be synthesized by conventional techniques including automated DNA synthesizers.

In some aspects, the N-intein fragment and the C-intein fragment and split toxin sequence (e.g., complementary split toxin sequences) are linked directly via a peptide bond. In some aspects, the fusion protein includes a spacer, or linker molecule between the N-intein fragment or C-intein fragment and the individual complementary split toxin sequences. Suitable spacer/linker molecules are known in the art.

In the fusion proteins described herein, the intein N-fragment can be fused either directly (e.g., via a peptide bond) or indirectly (e.g., via a linker amino acid sequence) to a split toxin sequence (e.g., a fragment). Thus, in some aspects, a split toxin sequence is fused either directly or indirectly to the N-terminus of an intein N-fragment. In some aspects, the first amino acid of the split toxin sequence can be selected from the group consisting of Met, Cys, Thr, Arg, Lys, Ser, Gin, His, Ala, Tyr, Phe, Asn, Trp, Val, Leu, Asp, He, Gly, Glu and Pro.

In some aspects, the fusion protein can comprise a linker between the split toxin sequence and the intein sequence. For example, the fusion protein can comprise a linker between the C-terminus of the split toxin sequence (e.g., a fragment) and the N-terminus of the N-fragment of the intein. The linker can be, for example, from about 1 to about 10 amino acids in length. In some aspects, the linker can be about 1 to about 5 amino acids in length. For example, the linker can contain 1, 2, 3, 4, or 5 amino acids. In some aspects, the last amino acid of the linker contacting the split toxin sequence and the N-terminus of the N-fragment of an intein can be selected from the group consisting of Met, Cys, Thr, Arg, Lys, Ser, Gin, His, Ala, Tyr, Phe, Asn, Trp, Val, Leu, Asp, He, Gly, Glu and Pro.

The fusion proteins described herein can optionally further include one or more detectable labels. Labels suitable for use according to the present disclosure are known in the art and generally include any molecule that, by its chemical nature, and whether by direct or indirect means, provides an identifiable signal allowing detection of a protein. Thus, for example, fusion proteins may be labeled in a conventional manner, such as with specific reporter molecules, fluorophores, radioactive materials, or enzymes (e.g., peroxidases, phosphatases). In some aspects, the fusion proteins can include one or more fluorescent dyes as detectable labels. Standard methods for modifying a protein to include a detectable label are known in the art.

Methods of Treating

Disclosed herein are methods of treating a human patient. In some aspects, the methods can comprise: administering one or more of the platelets disclosed herein to the patient. In some aspects, the methods can comprise: administering one or more of the engineered platelets disclosed herein to the patient. In some aspects, the patient has been identified as being in need of treatment before the administration step.

Also disclosed herein are methods of inducing apoptosis of a circulating tumor cell. In some aspects, the methods of inducing apoptosis of a circulating tumor cell. In some aspects, the methods can comprise: contacting a circulating tumor cell with one or more of the platelets disclosed herein. In some aspects, the contacting can be performed under conditions that permit a) binding of the intein fragment comprising the intein N-fragment to the intein fragment comprising the intein C-fragment to form an intein complex, wherein the intein complex is inactive, and b) binding of the split toxin sequence that is N-terminal to the intein N-fragment to the split toxin sequence that is C-terminal to the intein C-fragment to form a toxin complex, wherein the toxin complex is active; thereby inducing apoptosis of the circulating tumor cell. In some aspects, the circulating tumor cell expresses a cancer antigen. In some aspects, the cancer antigen can be Her-2.

In some aspects, the disease can be a cancer. In some aspects, the cancer can be a primary or secondary tumor. In some aspects, the cancer has metastasized. In some aspects, the cancer can be a solid cancer or a blood cancer. The cancer can be any cancer. In some aspects, the cancer can anal cancer, bladder cancer, brain cancer, bone cancer, breast cancer, cervical cancer, colorectal cancer, endocrine cancer, esophageal cancer, eye cancer, gallbladder cancer, head and neck cancer, kidney cancer, leukemia, liver cancer, lymphoma, melanoma, oral or oropharyngeal cancer, osteosarcoma, parathyroid cancer, pancreatic cancer, penile cancer, pituitary gland cancer, prostate cancer, skin cancer, stomach cancer, testicular cancer, thyroid cancer, uterine cancer, vulvar cancer, ovarian cancer, lung cancer, or gastric cancer.

Agonists and Dosage. The term "treatment," as used herein in the context of treating a disease or disorder, can relate generally to treatment and therapy of a human subject or patient, in which some desired therapeutic effect is achieved, for example, the inhibition of the progress of the disease or disorder, and can include a reduction in the rate of progress, a halt in the rate of progress, regression of the disease or disorder, amelioration of the disease or disorder, and cure of the disease or disorder. Treatment as a prophylactic measure (i.e., prophylaxis, prevention) is also included.

In some aspects, the platelets, engineered platelets or the population of platelets can be delivered in a therapeutically-effective amount.

The term "therapeutically-effective amount" as used herein, refers to the amount of the platelets that is effective for producing some desired therapeutic effect, commensurate with a reasonable benefit/risk ratio, when administered in accordance with a desired treatment regimen.

Similarly, the term "prophylactically effective amount," as used herein refers to the amount of the platelets that is effective for producing some desired prophylactic effect, commensurate with a reasonable benefit/risk ratio, when administered in accordance with a desired treatment regimen. "Prophylaxis" as used herein refers to a measure which is administered in advance of detection of a symptomatic condition, disease or disorder with the aim of preserving health by helping to delay, mitigate or avoid that particular condition, disease or disorder.

In some aspects, any of the platelets described herein can be administered via a transfusion to a subject or patient in any amount wherein the amount is sufficient to elicit a therapeutic response. In some aspects, the platelet concentration can be at least 1,000 μl, 5,000 or 10,000 μl or within a range of 1,000 μl to 5,000 μl, 5,000 μl to 10,000 μl or any amount in between.

Administration regimen" or "support regimen" can refer to a schedule of platelet administration comprising amounts and types of platelets or other cells administered in accordance with a determined mode (such as continuous or intermittent) at a specific rate wherein mode or rate may vary with time. "Optimized administration regimen" or "optimized support regimen" refers to an administration or support regimen that is optimized by selecting platelets in accordance with a molecular attribute of the intended recipient.

The term "pharmaceutically acceptable," as used herein, relates to compounds, ingredients, materials, compositions, dosage forms, etc., which are, within the scope of sound medical judgment, suitable for use in contact with the tissues of the subject (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

In some aspects, the disclosed methods or compositions can be combined with other therapies, whether symptomatic or disease modifying.

The term "treatment" includes combination treatments and therapies, in which two or more treatments or therapies are combined, for example, sequentially or simultaneously. For example it may be beneficial to combine treatment with a compound as described herein with one or more other (e.g., 1, 2, 3, 4) agents or therapies. Appropriate examples of co-therapeutics are known to those skilled in the art based one the disclosure herein. Typically the co-therapeutic can be any known in the art which it is believed may give therapeutic effect in treating the diseases or disorders described herein, subject to the diagnosis of the individual being treated. The particular combination would be at the discretion of the physician who would also select dosages using his/her common general knowledge and dosing regimens known to a skilled practitioner.

The agents (e.g., engineered platelet) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

Methods

Also disclosed herein are methods of producing red blood cells and platelets. The method can comprise the following steps. The method can include step a): providing a genetically engineered feeder cell. The feeder cell can include one or more genetic circuits. The one or more genetic circuits can include one or more genes of interest; and one or more promoters. The method can include step b): providing a genetically engineered fed cell. The fed cell can include one or more genetic circuits. The one or more genetic circuits can include one or more genes of interest; and one or more promoters. The one or more genes of interest can be different than the one or more genes of interest in a). The method can further include step c): culturing the genetically engineered feeder cell in a) with the genetically engineered fed cell in b). The culturing step can take place in a media under conditions that permit the genetically engineered fed cells to differentiate into red blood cells or platelets. The one or more of the genetically engineered fed cells as disclose herein can differentiate into red blood cells or platelets.

In some aspects, the one or more genetic circuits in method step a) disclosed herein can be regulatable. In some aspects, the one or more genetic circuits can be regulated by one or more genes of interest of the genetic circuit in the genetically engineered fed cell. In some aspects, the one or more genetic circuits as disclosed herein can be regulated by the one or more genes of interest of the genetic circuit in the genetically engineered feeder cell.

In some aspects, the one or more genetic circuits as disclosed herein an in step a) can be regulated by one or more promoters. In some aspects, the one or more genetic circuits in step a) can further include one or more recombinases. In some aspects, the one or more recombinases can be, for example Cre or phiC31 integrase or Bxb1 integrase. In some aspects, the one or more recombinases can be regulatable. In some aspects, the one or more genetic circuits as disclosed herein and in a) can further include one or more recombination sites. In some aspects, the one or more recombination sites can be loxP, attP or Bxb1. In some aspects, the attP sites can be inserted at Rosa26 locus and/or in chromosome 11.

As used herein, the term "promoter" refers to regulatory elements, promoters, promoter enhancers, internal ribosomal entry sites (IRES) and other elements that are capable of controlling expression (e.g., transcription termination signals, including but not limited to polyadenylation signals and poly-U sequences). Promoters can direct constitutive expression. Promoters can also direct expression in a temporal-dependent manner including but not limited to cell-cycle dependent or developmental stage-dependent. Examples of promoters include but are not limited to WPRE, CMV enhancers, and SV40 enhancers. Specific gene specific promoters can be used. Such promoters allow cell specific expression or expression tied to specific pathways. Any promoter that is active in mammalian cells can be used. In some aspects, the promoter is an inducible promoter including, but not limited to, Tet-on and Tet-off systems. Such inducible promoters can be used to control the timing of the desired expression. In some aspects, the promoter can be an inducible promoter. Examples of inducible promoters include but are not limited to tetracycline inducible system (tet); heat shock promoters and IPTG activated promoters. In some aspects, promoters are bidirectional.

The promoter and/or enhancer can be specifically activated either by light or specific chemical events which trigger their function. Systems can be regulated by reagents such as tetracycline and dexamethasone.

In some aspects, the genetic circuits as disclosed herein can comprise a promoter, for example but not limited to, enhancers, 5' untranslated regions (5'UTR), 3' untranslated regions (3'UTR), and repressor sequences; constitutive promoters, inducible promoter; tissue specific promoter, cell-specific promoter or variants thereof. Examples of tissue-specific promoters include, but are not limited to, albumin, lymphoid specific promoters, T-cell promoters, neurofilament promoter, pancreas specific promoters, milk whey promoter; hox promoters, α-fetoprotein promoter, human LIMK2 gene promoters, FAB promoter, insulin gene promoter, transphyretin, alpha.1-antitrypsin, plasminogen activator inhibitor type 1 (PAI-1), apolipoprotein myelin basic protein (MBP) gene, GFAP promoter, OPSIN promoter, NSE, Her2, erb2, and fragments and derivatives thereof. Examples of other promoters include, but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and variants thereof.

The one or more genetic circuits disclosed herein and in step a) can further include one or more repressor proteins. In some aspects, the one or more repressor proteins can be Lad, TetR, and/or QS. In some aspects, the one or more repressor proteins disclosed herein can be regulatable.

The media can further include one or more modulators. In some aspects, the one or more modulators can modulate (e.g., repress or activate) the genetic circuits of a) or b) as disclosed herein. In some aspects, the one or more genetic circuits disclosed herein an in step a) can be regulated by one or more media modulators. In some aspects, the one or more media modulators can be isopropyl β-D-1-thiogalactopyranoside (IPTG), tetracycline, doxycycline, quinic acid, or auxin.

The method disclosed herein can also include one or more genetic circuits in step a) that are non-regulatable. In some aspects, the one or more promoters of the genetic circuits as disclosed herein and in step a) can be constitutively expressed. In some aspects, the one or more promoters of the genetic circuits disclosed herein and in step a) can be CMV, RSV and/or U6, beta actin, and/or elongation factor promoters. In some aspects, the one or more promoters can include one or more operator sites (e.g., tet). Such operator sites can allow for one or more repressor proteins to bind.

The method disclosed herein can also include one or more genes of interest of the genetic circuits in step a). In some aspects, the one or more genes of interest of the genetic circuits disclosed herein can be erythropoietin, thrombopoietin, and/or IL1-α. In some aspects, the one or more genes of interest of the genetic circuits disclosed herein and in step a) can be constitutively expressed.

The method disclosed herein can include a genetically engineered feeder cell. In some aspects, the genetically engineered feeder cell can be derived from an embryonic stem cell or a mouse embryonic stem cell. In some aspects, the genetically engineered feeder cell can be an osteoblast. In some aspects, the osteoblast can be an OP-9 stromal cell. In some aspects, the osteoblast can be from cord blood or bone marrow. In some aspects, the genetically engineered feeder cell can be derived from an immortalized cell line. In some aspects, the genetically engineered feeder cell can support undifferentiated hematopoietic stem cell (HSC) growth. In some aspects, the genetically engineered feeder cell is capable of being genetically engineered.

The method disclosed herein can include a non-genetically engineered feeder cell. In some aspects, the feeder cell can be derived from an embryonic stem cell or a mouse embryonic stem cell. In some aspects, the feeder cell can be an osteoblast. In some aspects, the osteoblast can be an OP-9 stromal cell. In some aspects, the osteoblast can be from cord blood or bone marrow. In some aspects, the feeder cell can be derived from an immortalized cell line. In some aspects, the feeder cell can support undifferentiated hematopoietic stem cell (HSC) growth.

The methods disclosed herein can use a variety of cells. Examples of cells include but are not limited to stem cells, such as embryonic stem cells.

The method disclosed herein can include one or more genetic circuits as described herein and in b) that can be regulatable. In some aspects, the one or more genetic circuits in b) can be regulated by one or more genes of interest of the genetic circuit in the genetically engineered fed cell. In some aspects, the one or more genetic circuits in b) can be regulated by one or more genes of interest of the genetic circuit in the genetically engineered feeder cell. In some aspects, one or more genetic circuits in b) can further comprise one or more recombinases. In some aspects, one or more recombinases can be Cre or phiC31 integrase or Bxb1 integrase. In some aspects, one or more recombinases can be regulatable.

The method disclosed herein can include one or more genetic circuits as described herein and in step b) that further comprise one or more recombination sites. In some aspects, one or more recombination sites can be loxP, attP or Bxb1. In some aspects, the attP, loxP, or Bxb1 sites can be inserted at Rosa26 locus. In some aspects, the one or more genetic circuits disclosed herein and in step b) can be regulated by one or more promoters. In some aspects, one or more genetic circuits disclosed herein and in step b) can further comprise one or more repressor proteins. In some aspects, one or more repressor proteins can be Lad, TetR, or QS. In some aspects, one or more repressor proteins can be regulatable.

In some aspects, one or more genetic circuits disclosed herein and in step b) can be regulated by one or more media modulators. In some aspects, one or more modulators can be isopropyl β-D-1-thiogalactopyranoside (IPTG), tetracycline, doxycycline, quinic acid, or auxin. Such media modulators or agents are well known in the art.

The method disclosed herein can include one or more genetic circuits described herein and in step b) that can be non-regulatable. In some aspects, one or more promoters of the genetic circuits disclosed herein and in step b) can be constitutively active. In some aspects, one or more promoters of the genetic circuits in step b) can be CMV, RSV U6, beta actin, and/or elongation factor promoters. In some aspects, one or more promoters (e.g., CMV, RSV and/or U6) can comprise one or more operator sites. In some aspects, the operator sites can allow for repressor proteins to bind.

In some aspects, one or more genes of interest of the genetic circuits disclosed herein and in step b) can be HoxB4 and/or GATA-1. In some aspects, one or more genes of interest of the genetic circuits disclosed herein and in step b) can be constitutively expressed. In some aspects, GATA-1 comprises an auxin protein degradation tag.

In some aspects, the genetically engineered fed cells described herein can be hematopoietic progenitor stem cells. In some aspects, the hematopoietic stem cell can be derived from cord blood, bone marrow, iPS cell, or ES cell. In some aspects, the genetically engineered fed cell can be capable of producing progenitor cells of platelets and red blood cells. In some aspects, the progenitor cells can be capable of producing platelets and red blood cells. In some aspects, the progenitor cells can comprise one or more of the genetic circuits disclosed herein. In some aspects, the progenitor cells comprise one or more of the genetic circuits disclosed herein that can regulate the expression of any of the one or more genes of interest. In some aspects, one or more genes of interest can be HoxB4 and/or GATA-1. In some aspects, the genetic circuits described herein also can comprise one or more repressor proteins (e.g., Lad, TetR or QS) and can be controlled by one or more medial modulators (e.g., isopropyl β-D-1-thiogalactopyranoside (IPTG), tetracycline, doxycycline, quinic acid, or auxin).

The gene of interest can be any gene. It can be endogenous or introduced. The terms "target," "target gene," and "target nucleotide sequence" can be used interchangeably and refers to the gene of interest. For example, a target gene is a gene of known function or is a gene whose function is unknown, but whose total or partial nucleotide sequence is known. Alternatively, the function of a target gene and its nucleotide sequence are both unknown. A target gene can be a native gene of the eukaryotic cell or can be a heterologous gene which has previously been introduced into the eukaryotic cell or a parent cell of said eukaryotic cell, for example by genetic transformation. A heterologous target gene can be stably integrated in the genome of the eukaryotic cell or is present in the eukaryotic cell as an extrachromosomal molecule, e.g., as an autonomously replicating extrachromosomal molecule. A target gene can include polynucleotides comprising a region that encodes a polypeptide or polynucleotide region that regulates replication, transcription, translation, or other process important in expression of the target protein; or a polynucleotide comprising a region that encodes the target polypeptide and a region that regulates expression of the target polypeptide; or non-coding regions such as the 5' or 3' UTR or introns. A target gene may refer to, for example, an mRNA molecule produced by transcription a gene of interest. The design or construction of the genetic circuits disclosed herein can be carried out in a modular fashion, allowing for the regulation of any gene, including heterologous and other recombinant genes. In some aspects, the parts or modules can be genetic activators, genetic repressors, recombinases, genome editing, and synthetic transcription factors. In some aspects, the genetic circuit described herein can comprise one or more modules.

Vectors can be introduced in a prokaryote, amplified and then the amplified vector can be introduced into a eukaryotic cell. The vector can also be introduced in a prokaryote, amplified and serve as an intermediate vector to produce a vector that can be introduced into a eukaryotic cell (e.g., amplifying a plasmid as part of a viral vector packaging system). A prokaryote can be used to amplify copies of a vector and express one or more nucleic acids to provide a source of one or more proteins for delivery to a host cell or host organism. Expression of proteins in prokaryotes is often carried out in *Escherichia coli* with vectors containing constitutive or inducible promoters directing the expression of either fusion or non-fusion proteins. Vectors can also be a yeast expression vector (e.g., *Saccharomyces cerevisiae*).

In some aspects, the vector is capable of driving expression of one or more sequences in mammalian cells using a mammalian expression vector. Examples of mammalian expression vectors include but are not limited to pCDM8 and pMT2PC. In mammalian cells, regulatory elements control the expression of the vector. Examples of promoters are those derived from polyoma, adenovirus 2, cytomegalovirus, simian virus 40, and others disclosed herein and known in the art.

In some aspects, the methods disclosed herein can include conditions in step c) that permit the expression of one or more genes of interest in steps a) or b). In some aspects, osteoblasts can be contacted, exposed to or treated with mitomycin-C. The osteoblasts can be washed before the stem cells are added. The osteoblasts can be washed to remove the mitomycin-C. Generally, the osteoblasts can be prepared accordingly to standard protocol that is known to one of ordinary skill in the art. The osteoblasts, for example, can be treated with mitomycin-C prior to or just before growing additional cells on top of the feeder cells.

In some aspects, the medium that can be used in the methods disclosed herein can comprise one or more components or modulators (e.g., media modulators). The one or more components or modulators can lead to the formation of platelet and/or red blood cell progenitor stem cells. In some aspects, one or more components or modulators described herein can be isopropyl β-D-1-thiogalactopyranoside (IPTG), tetracycline, doxycycline, quinic acid, or auxin. In some aspects, the progenitor stem cells can produce platelet and/or red blood cell precursor cells. In some aspects, the progenitor stem cells can express one or more self-identifying cell surface markers. In some aspects, the progenitor stem cells can express GATA-1 and/or HoxB4. In some aspects, the expression of one or more cell surface markers can be produced by the genetic circuit disclosed herein. In some aspects, the one or more cell surface markers can be self-identifying. In some aspects, one or more cell surface markers can be CD13, CD34, CD41a, and CD43.

In some aspects, the platelets and/or red blood cells produced by the method described herein can express one or more cell surface markers. In some aspects, one or more cell surface markers can be CD41a and CD42b.

In some aspects, the method disclosed herein can further comprise step d): isolating or purifying the platelets or red blood cells.

Methods of Treating

Disclosed herein are methods of treating a patient. In some aspects, the patient can be in need of a platelet transfusion. In some aspects, the methods can comprise administering a therapeutically effective amount of the in vitro produced and optionally isolated platelets. The in vitro produced and optionally isolated platelets can be produced by any of the methods disclosed herein.

Disclosed herein are methods of producing platelets comprising a therapeutic agent, peptide, enzyme or bioactive molecule (biomolecule). In some aspects, the methods can comprise any of the methods disclosed herein to produce platelets harboring therapeutic proteins within them to be released in the body. In some aspects, the methods can comprise extrinsic and/or intrinsic regulation as described herein. In some aspects, the methods can also include engineering the platelets to comprise receptors capable of activating the platelets to trigger the release of, for example, enzymes upon binding to specific drugs and/or binding to tissue specific peptides.

Disclosed herein are methods of producing platelets comprising therapeutic agents, peptide, enzyme or bioactive molecule (biomolecules). In some aspects, the methods can comprise the steps: a) providing a genetically engineered osteoblast; b) providing a genetically engineered hematopoietic stem cell (HSC), wherein the HSC comprises one or more genetic circuits; wherein the one or more genetic circuits comprise one or more genes of interest, wherein the one or more genes of interest are different than the one or more genes of interest in a); and one or more promoters; c) culturing the genetically engineered osteoblast in a) with the genetically engineered HSC in b) in a media under conditions that permit the genetically engineered HSC to differentiate into platelet stem cells; and d) producing platelets comprising therapeutic agents, peptide, enzyme or bioactive molecule. In some aspects, the platelets that are produced can comprise an engineered receptor or a modified receptor. In some aspects, the genetically engineered HSC can be from a pluripotent stem cells or one of their progenitor stem cells. The progenitor stem cells are capable of producing the therapeutic agent, peptide, enzyme or bioactive molecule. The progenitor stem cells can be regulated intrinsically or extrinsically to produce or secrete the therapeutic agent, peptide, enzyme or bioactive molecule. The methods can also include engineering the platelets to comprise receptors capable of activating platelets to trigger the release of enzymes upon binding to specific drugs and/or binding to tissue specific peptides.

As used herein, the term "therapeutic agent" refers to a chemical compound, a protein, a peptide, a small molecule, an antibody, a gene, an enzyme or a cell.

In some aspects, the therapeutic proteins or agents as disclosed herein can be transcribed from genetic circuits in platelet progenitor stem cells, prior to the terminal differentiation into platelets. In some aspects, the therapeutic proteins or agents as disclosed herein can be transcribed from genetic circuits in megakaryocytes. These therapeutic proteins or agents can be present in the cytoplasm of progenitor cells and, therefore, be a part of the terminally differentiated platelets. The production of therapeutic proteins or agents can be transcribed from constitutively expressing promoters, and/or with inducible genetic circuits.

In some aspects, the method disclosed herein can further comprise the step: e) re-culturing the progenitor stem cells produced step c) in a media under conditions promoting the differentiation of the progenitor stem cells into platelets. In some aspects, the method disclosed herein can further comprise the step: f) collecting or isolating the platelets.

In some aspects, the methods disclosed herein can be carried out to produce therapeutic cells. Therapeutic cells can comprise one or more therapeutic agents, peptides, enzymes, genes or bioactive molecule. In some aspects, the therapeutic agent can be a small molecule, a gene, a peptide, an enzyme, a vaccine, or an antimicrobial.

In some aspects, the one or more genetic circuits in a) are regulatable. In some aspects, the one or more genetic circuits in a) can be regulated by the one or more genes of interest of the genetic circuit in the genetically engineered HSC. In some aspects, the one or more genetic circuits in a) can be regulated by one or more promoters. In some aspects, the one or more promoters of the genetic circuit in a) and b) can be CMV, RSV and/or U6. In some aspects, the one or more promoters (e.g., CMV, RSV and/or U6) can comprise an operator site (e.g., tet).

In some aspects, the one or more genetic circuits in a) can further comprise one or more recombinases. In some aspects, the one or more recombinases can be Cre, phiC31 integrase and/or Bxb1. In some aspects, the one or more recombinases can be regulatable. In some aspects, the one or more genetic circuits in a) can further comprise one or more recombination sites. In some aspects, the one or more recombination sites can be loxP or attP. In some aspects, the attP or any other recombinase recognition sites can be inserted at Rosa26 and/or chromosome 11 locus. In some aspects, the attP and any other integrase recognition cites can serve as the insertion site for the therapeutic agent.

In some aspects, the one or more genetic circuits in a) can further comprise one or more repressor proteins. In some aspects, the one or more repressor proteins can be Lad, TetR, and/or QS. In some aspects, the one or more repressor proteins can be regulatable.

In some aspects, the media disclosed herein can further comprise one or more components or modulators. In some aspects, the one or more genetic circuits in a) and b) can be regulated by one or more media modulators or components. In some aspects, the one or more media modulators or components can be isopropyl β-D-1-thiogalactopyranoside (IPTG), tetracycline, doxycycline, quinic acid, or auxin.

In some aspects, the one or more genes of interest of the genetic circuit in a) can be thrombopoietin. In some aspects, thrombopoietin can be constitutively expressed.

In some aspects, the one or more genetic circuits in b) can be regulatable. In some aspects, the one or more genetic circuits in b) can be regulated by the one or more genes of interest of the genetic circuit in the genetically engineered HSC. In some aspects, the one or more genetic circuits in b) can be regulated by one or more promoters. In some aspects, the one or more promoters of the genetic circuit in b) can be CMV, RSV and/or U6.

In some aspects, the one or more genetic circuits in b) can further comprise one or more recombinases. In some aspects, the one or more recombinases can be phiC31 integrase or Cre or Bxb1 integrase. In some aspects, the one or more recombinases can be regulatable. In some aspects, the one or more genetic circuits in b) can further comprise one or more recombination sites. In some aspects, the one or more recombination sites can be loxP, attP or Bxb1. In some aspects, the attP, loxP or Bxb1 sites can be inserted at Rosa26 locus. In some aspects, the one or more recombination sites can serve as the insertion site for the therapeutic agent.

As described herein, the recombinase sites in the genome, for example, attP, can be used to insert any of the genetic circuits disclosed herein into the genome via a 'docking site.' This docking site allows for the targeted and robust insertion of the genetic circuits disclosed herein into the genome that are known to be robust in achieving gene expression and can be resistant to epigenetic silencing.

The location of the therapeutic agent can be in the genome.

In some aspects, the one or more genetic circuits in b) can further comprise one or more repressor proteins. In some aspects, the one or more repressor proteins can be Lad, TetR, and/or QS. In some aspects, one or more repressor proteins can be regulatable.

In some aspects, the media disclosed herein can further comprise one or more media modulators. In some aspects, the one or more media modulators can be isopropyl β-D-1-thiogalactopyranoside (IPTG), tetracycline, doxycycline, quinic acid, or auxin.

In some aspects, the one or more genes of interest of the genetic circuit in b) can be GATA-1. In some aspects, GATA-1 can be constitutively expressed.

In some aspects, the platelet progenitor stem cells in step c) can express one or more cell surface markers. In some aspects, the platelet progenitor stem cells in step c) can express GATA-1. In some aspects, the one or more surface markers can be CD13, CD34, CD41a, and CD43. In some aspects, the platelets or red blood cells can express one or more cell surface markers. In some aspects, the one or more cell surface markers can be CD41a and CD42b.

Disclosed herein are methods of treating a patient in need of a therapeutic agent. The method can comprise administering a therapeutically effective amount of therapeutic platelets to the subject or patient. The method can comprise identifying a patient in need of treatment before the administration step. The method can comprise administering to the patient a therapeutically effective amount of the isolated platelets. In some aspects, the platelets comprise a therapeutic agent. The isolated platelets and red blood cells do not contain DNA. These cells express the proteins and peptides that they were engineered to express via the methods disclosed herein. These cells are anucleated.

Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of condition disorder or disease.

The platelets as well as the platelets and red blood cells comprising a therapeutic agent described herein can be administered to the subject (e.g., a human patient) in an amount sufficient to delay, reduce, or preferably prevent the onset of clinical disease. Accordingly, in some aspects, the patient is a human patient. In therapeutic applications, compositions are administered to a subject (e.g., a human patient) already with or diagnosed with a condition, disorder or disease in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a platelets as well as the platelets comprising a therapeutic agent described herein can be an amount that achieves a cure, but that outcome is only one among several that can be achieved. One or more of the symptoms can be less severe. Recovery can be accelerated in an individual who has been treated.

The therapeutically effective amount of one or more of the therapeutic agents present within the platelets described herein and used in the methods as disclosed herein applied to mammals (e.g., humans) can be determined by one of ordinary skill in the art with consideration of individual differences in age, weight, and other general conditions (as mentioned above).

The platelets including platelets comprising a therapeutic agent described herein can be formulated for administration by any of a variety of routes of administration.

The platelets including platelets comprising a therapeutic agent can be prepared for parenteral administration. Platelets prepared for parenteral administration includes those prepared for intravenous (or intra-arterial), intramuscular, subcutaneous, and intraperitoneal, administration.

Any of the genetic circuits or nucleic acid constructs described herein can be used with any of the cells or any of the methods disclosed herein.

EXAMPLES

Figures 3A, 3B:
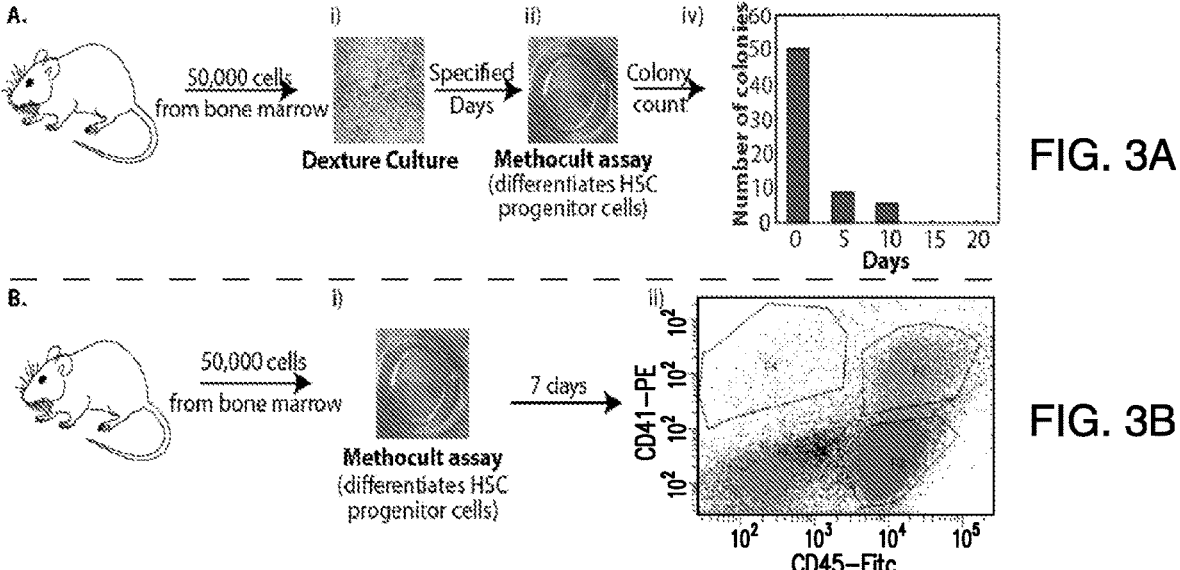
FIGS. 3A-D shows a method of assessing HSC growth and potential.
Figures 3C, 3D:
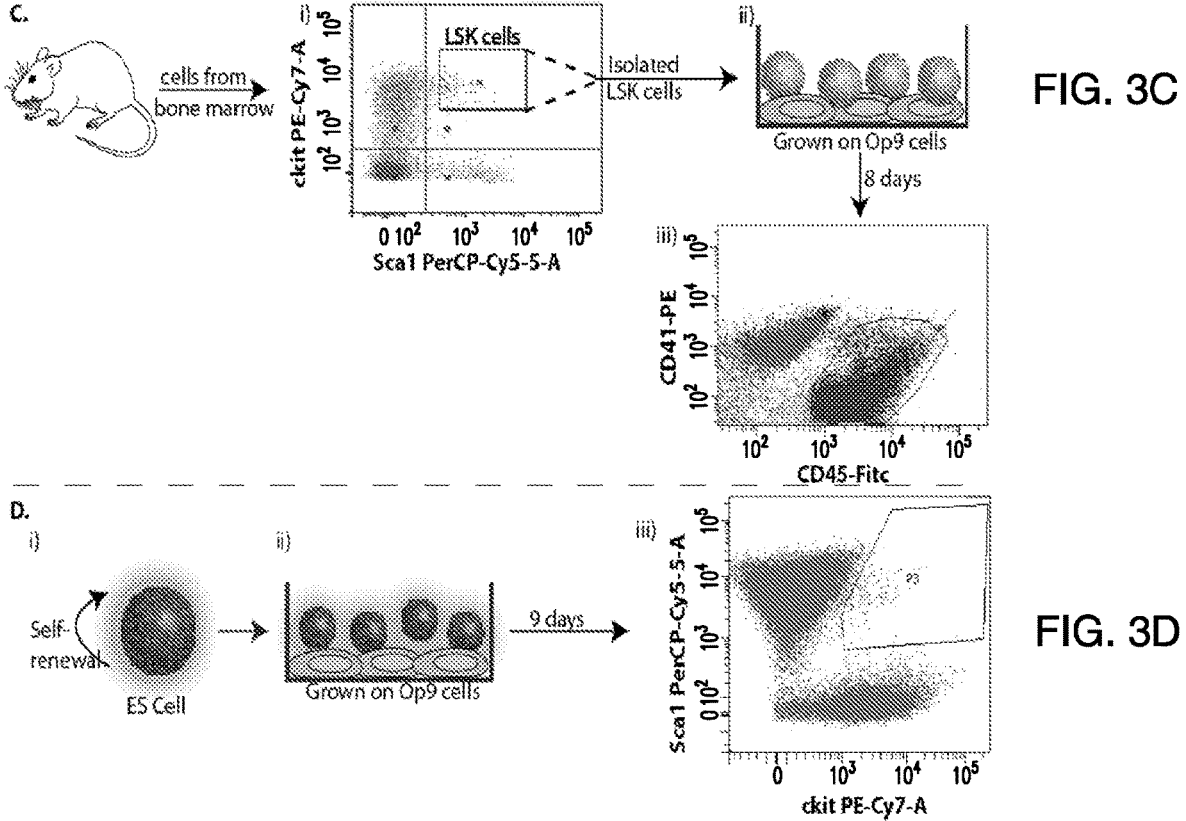
Figures 4A, 4B, 4C:
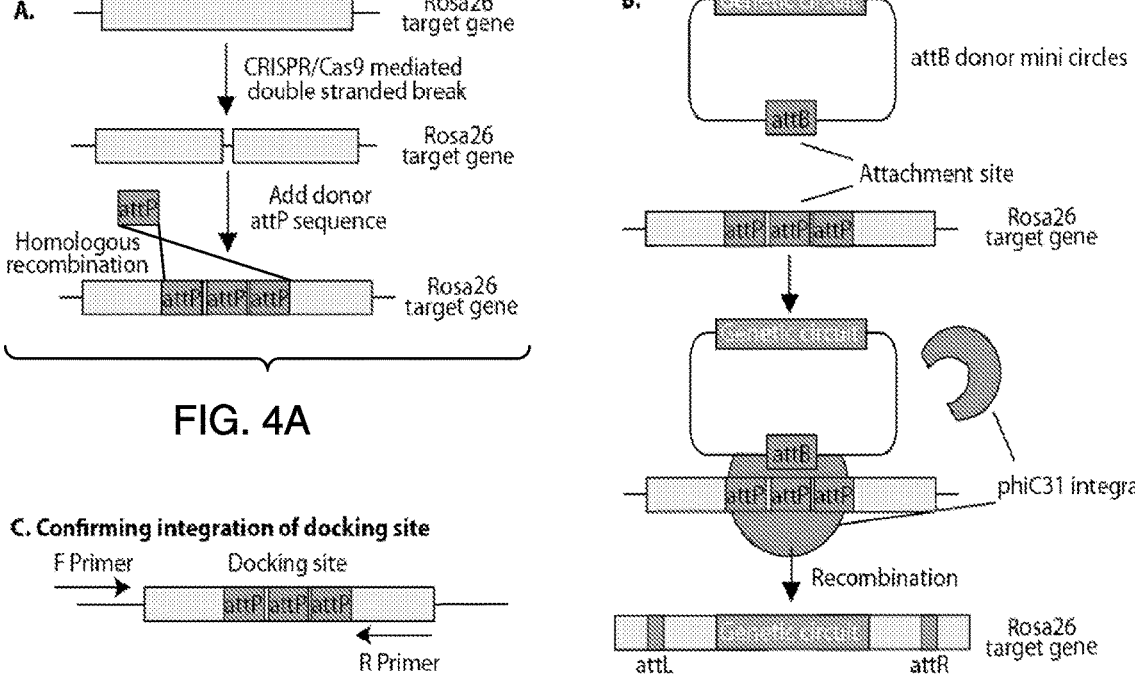
FIGS. 4A-D shows Landing pad in Rosa26 locus.

Example 1: Engineer Pluripotent Stem Cells to Regulate the Intrinsic Cues for Enhanced Differentiation To determine whether mouse HSCs provide an adequate cell source for using the genetic tools, tools and methods were developed to load platelets, whole bone marrow was removed from mice and tested for long-term potential (FIG. 3A). Consistent with other reports, the number of lineage-committed HSC progenitors significantly decline over time (Mootz H D, Muir T W. *Journal of the American Chemical Society* 2002; 124(31): 9044-5; Schwartz E C, et al. *Nature chemical biology* 2007; 3(1): 50-4; Selgrade D F, et al. *Journal of the American Chemical Society* 2013; 135(20): 7713-9; Tyszkiewicz A B, Muir T W. Activation of protein splicing with light in yeast. *Nature methods* 2008; 5(4):

303-5; Zeidler M P, et al. *Nature biotechnology* 2004; 22(7): 871-6; and Deans T L, et al. *Cell* 2007; 130(2): 363-72) (FIG. 3B). Next, to determine whether isolated HSCs from the bone marrow could be differentiated into platelets in vitro, multipotent HSCs (LSK+ cells) were isolated from mouse bone marrow and differentiated them using standard differentiation conditions (Deans T L, et al. *Proceedings of the National Academy of Sciences of the United States of America* 2012; 109(38): 15217-22; Singh A, et al. *Acs Macro Letters* 2013; 2(3): 269-72; and Fitzgerald M, et al. Synthetic Biology 2020) (FIG. 3C). From these studies, it was concluded that because HSCs have such a short lifetime in culture, genetically manipulating them directly for these purposes is not realistic. Next, the efficacy of differentiating embryonic stem cells (ES) into multipotent HSCs in vitro was tested and it was found that multipotent HSCs (LSK+) cells could be obtained within 9 days of culturing (FIG. 3D). Therefore, mouse embryonic stem (ES) will be genetically manipulated because these cells proliferate quickly, they renew their pluripotent cell population consistently, and they are easy to maintain in culture. These genetically manipulated ES cells will be differentiated into HSCs. Another advantage of this ES cell approach is that the engineered cells can be rapidly expanded and maintained longer than alternative cell lines such as primary HSCs, which rapidly reach senescence or spontaneously differentiate and therefore have a shorter functional lifetime. To accomplish this, a modular technology that utilizes CRISPR technology to insert a 'landing pad' or 'docking site' for genetic circuits was implemented. Conventional techniques involve the random insertion of genetic circuits into the genome, selecting stable clones in which the circuit is stably integrated, and testing the functionality of the circuit at that particular insertion site. These steps can be tedious and time consuming. Furthermore, the testing phase is significant because each clone may be different and positional affects (e.g. due to local enhancers, repressors, or epigenetic modifications) that may lead to the deregulation or misregulation of the circuit. To bypass these limitations, mouse embryonic stem (ES) cells have been engineered with 'docking sites' in the Rosa26 locus to allow for targeted and robust insertion of genetic circuits. The Rosa26 locus is widely used for achieving robust gene expression in mouse models and is resistant to epigenetic silencing (Fitzgerald M, et al. *ACS synthetic biology* 2017; 6(11): 2014-20). Using CRISPR/Cas9 technology, three attP sites have been added to the Rosa26 locus (FIG. 4), which allows unidirectional recombination at these sites to insert genetic circuits specifically at this locale using phiC31 integrase (FIG. 4B) (Bush L, Marvin J, Deans T L. Combination image flow cytometry for rare single-cell event analysis. bioRxiv 2019; doi: doi.org/10.1101/512442). This allows a robust methodology for inserting any gene network into the genome of mouse ES cells. Furthermore, because ES cells are totipotent, these genetically modified cells can be differentiated into a range of different functional cell types based upon the disease or tissue of interest. For the purpose of platelet production and producing lysosomal enzymes in MKs, genetically altered ES cells will be differentiated into HSCs and the expression of lysosomal enzymes will be controlled at different stages throughout differentiation. Furthermore, developing this technology allows for any genetic background of cell type to be used and ensures immune compatibility with the various mouse models that are used. Finally, use of CRISPR technology will allow similar docking sites to be built in human cell lines.

Example 2: Genetically Engineer Megakaryocytes to Create Platelets that Secrete Biomolecules Platelets possess many characteristics that make them attractive candidates for in vivo delivery of natural and synthetic payloads: 1) they have extensive circulation range in the body, 2) they are a nucleated cells, 3) they are biocompatible, 4) their average lifespan in humans is ~10 days, and 5) following activation, their protein granules serve as secretory vesicles, releasing components to the extracellular fluid. By using synthetic biology as disclosed herein, MKs can be programmed to express therapeutic levels of protein cargo to be targeted for platelet secretion. As a proof of concept, enhanced green fluorescence protein (EGFP), secreted alkaline phosphatase (SEAP), and luciferase will initially be expressed in MKs to determine the efficacy of using platelets as delivery vehicles for therapeutic payloads. This suite of reporter molecules has been selected because they can be used to assay different aspects of the cargo loading and delivery process. EGFP will be used to determine if soluble transgenic cargos are packaged into secretory granules, SEAP will be used to assay the extent of cargo release into the media of cells grown in vitro, and luciferase will be used to determine whether engineering platelets are enriched to sites of injury similar to endogenous platelets, to be used once these studies are moved to in vivo models.

Figure 4D:
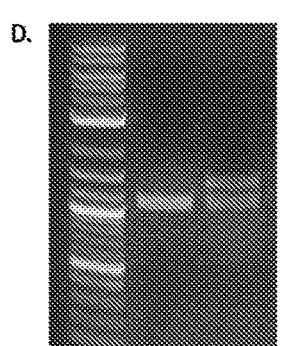

Experiments and methodology. As a proof of concept to use platelets as delivery vehicles for therapeutic biomolecules, constitutively expressing reporter genes will be inserted into the attP site of ES cells (FIG. 4). These cells will be plated on OP9 stromal support cells and differentiated into MKs using the previously described. The attP landing pad in ES cells will be used that were engineered to insert constitutively expressing reporter genes, differentiate these cells into MKs and platelets, then assay these cells for reporter expression to determine the location and function of these recombinantly made proteins and how they affect platelet function.

Express GFP in MKs and platelets: Like many potential bio-therapeutic molecules, GFP is a small, soluble protein that diffuses throughout the cytoplasm. MKs will be harvested for FACS analysis to confirm MK differentiation, and GFP expression level. The percent of GFP expressing MKs in the whole population will also be assessed. After determining the GFP expression level in MKs, MKs expressing GFP will be differentiated into platelets. FACs analysis will be done to confirm platelet differentiation and to quantify the GFP expression in these cells. In order to establish the sub-cellular distribution of GFP in platelets purified cells will be immunolabeled using antibodies against GFP.

Express SEAP in MKs and platelets: After differentiating HSCs to MKs on a layer of OP9 stromal cells, these cells will be harvested and SEAP secretion will be quantified in the media using established ELISA protocols (Weisenberger M S, Deans T L. *J Ind Microbiol Biotechnol* 2018; 45(7): 599-614). After determining SEAP secretion from MKs, the MKs expressing SEAP will differentiate into platelets and it will be determined whether platelets are capable of secreting biomolecules in vitro. To accomplish this, the engineered platelets will be characterized with non-engineered platelets by testing levels of SEAP in the culture media over multiple time points (three times a day for 10 days).

Express luciferase in MKs and platelets: To determine whether the engineered platelets are capable of responding to injury, luciferase will be expressed in MK cells and platelets, which will allow for live animal imaging. These experiments will serve as proof of concept for engineering platelets that are capable of expressing luciferase. After differentiating HSCs into MKs, luciferase activity will be quantified using a plate reader that is capable of biolumi-nescence.

Platelet characterization. Platelet cell differentiation can be identified by surface markers using flow cytometry. Degranulation and aggregation assessments will be made with respect to known activators von Willebrand Factor (vWF) (Scott A M, et al. *Cancer Immun* 2012; 12: 14), fibrinogen (Ito Y, et al. *Cell* 2018; 174(3): 636-48 e18), collagen (Avanzi M P, et al. *Transfusion* 2016; 56(1): 170-8; and Blin A, Le Goff A, Magniez A, et al. Microfluidic model of the platelet-generating organ: beyond bone marrow bio-mimetics. *Sci Rep* 2016; 6: 21700), and thrombin (Di Buduo C A, et al. *Blood* 2015; 125(14): 2254-64). Platelet degranu-lation will be determined by ELISA specific to serotonin and platelet derived factor 4 (PDF-4) (Nakagawa Y, et al. *Exp Hematol* 2013; 41(8): 742-8). As a control, freshly isolated platelets from mice will be used for comparison. Platelet ability to aggregate in the presence of known activators will be determined using an aggregometer. Additionally, platelet degranulation by thrombin, which acts by enzymatically cleaving PAR receptors on platelets (Di Buduo C A, et al. *Blood* 2015; 125(14): 2254-64), will be determined by ELISA specific to serotonin and platelet derived factor 4 (PDF-4) (Nakagawa Y, et al. *Exp Hematol* 2013; 41(8): 742-8).

In the event that GFP is not expressed in platelets, myristol-tagged GFP that has been shown to associate with the cell membrane (Thon J N, et al. *The Journal of cell biology* 2010; 191(4): 861-74) will be used. In this case, the GFP will associate with the MK membrane and is likely to become a part of the platelet membrane. Microscopy and flow cytometry will be done to observe and quantify GFP expression. In the event that SEAP or luciferase are not a part of the platelets, the reporter genes can be tagged with the amino acid sequence, LKNG (SEQ ID NO: 1), which has been demonstrated to be directly involved in the targeting and/or storage of the megakaryocytic proteins (Rhee J M, et al. *Genesis* 2006; 44(4): 202-18). To accomplish this, LKNG (SEQ ID NO: 1) can be fused to the reporter molecules in either the 5' or 3' UTR to be targeted for granule packaging in MKs.

Example 3: Develop and Validate Directed Evolution Approaches for Engineering Novel Platelet Receptors Platelets can become activated to secrete their bioactive molecules via G-protein coupled receptor (GPCR) signaling (El Golli N, et al. *The Journal of biological chemistry* 2005; 280(34): 30329-35). GPCRs are a large family of versatile membrane proteins that have been the focus of many thera-peutic targets because of their involvement in a range of normal and pathological diseases. To obtain precise spa-tiotemporal control of GPCR signaling in vivo, Designer Receptors Exclusively Activated by Designer Drugs (DREADDs) have been engineered to selectively, rapidly, reversibly, and dose-dependently control behaviors and physiological processes in the mammalian brain (Deans T L, Elisseeff J H. *Current opinion in biotechnology* 2009; 20(5): 537-44). These engineered receptors have been designed to have no endogenous ligand, no background activity in the absence of the ligand, and an otherwise pharmacologically inert compound exclusively and potently activates the GPCR by nanomolar concentrations of pharmacologically inert and metabolically stable small molecules (Deans T L, Elisseeff J H. *Cell Stem Cell* 2010; 6(6): 499-501). Since platelets use GPCRs as one of their means of activation, it is possible to engineer DREADDs on platelets as a strategy for spatially and temporally controlling the activation of these cells.

Experiments and Methodology. DREADDs have previ-ously been engineered to enable non-invasive control of neuron signaling through the $G_q$, $G_i$, and $G_s$ G-protein coupled signaling pathways. To engineer receptors that are activated by a synthetic ligand and possess no biological activity, the GPCRs responsible for activating platelets will be modified to favor synthetic over endogenous substrate/ligand recognition. At the forefront of such modified GPCRs are the protease-activated receptors (PARs), which couple to $G_q$, $G_{12}/G_{13}$ and in some cases the G family of G proteins. PARs are activated by thrombin, the most effective activator of platelets (El Golli N, et al. *The Journal of biological chemistry* 2005; 280(34): 30329-35). Of the four PARs, PAR1 and PAR4 are present on human platelets, whereas mouse platelets express PAR3 and PAR4 (El Golli N, et al. *The Journal of biological chemistry* 2005; 280(34): 30329-35). For this reason, a directed molecular evolution approach will be taken to facilitate the creation of a family of PARs to be activated by the pharmacologically inert compound clozapine-N-oxide (CNO) but not by its native ligand throm-bin. For these studies, CNO will be used as the synthetic ligand because the most widely used DREADDs today use CNO as their ligand and studies have shown that it is a pharmacologically inert molecule lacking affinity for innate receptors, and activates spatial and temporal control of GPCR signaling at nanomolar concentrations (Deans T L, Elisseeff J H. *Current opinion in biotechnology* 2009; 20(5): 537-44; and Deans T L, Elisseeff J H. The life of a cell: probing the complex relationships with the world. *Cell Stem Cell* 2010; 6(6): 499-501).

Directed molecular evolution is a technique for endowing a particular property to a protein by successive rounds of random mutation, screening, and then selection. Success-fully evolving a protein to meet the desired criteria depends on several aspects of the experimental design including the biological diversity and size of the library to be screened, the quality of the screening assay, and the size of the functional jump from the template to the desired result. In the case of PAR receptors, which primarily engage the $G_q$ signaling pathways, it is anticipated that a few to moderate functional steps will be carried out to evolve these receptors for CNO to activate signaling since the original DREADDs targeted receptors also signal via the $G_q$ signaling pathways. In addition to designer drugs, it is also possible to evolve a receptor to respond to other drugs or to tissue specific peptides that would activate platelets and thus release their biological payloads upon binding to that tissue.

The experimental procedure for creating DREADDs is reported to be fairly straightforward. In short, the receptor of choice is randomly mutated to create a library of many different mutants, test the interactions of CNO with new mutant receptors, select mutants that are capable of binding to CNO, go through more rounds of random mutation to select for mutants that have even better interactions with CNO, select the best mutant candidate to be expressed in mammalian cells to then perform the binding assay.

If it is not possible to get GPCR expression in yeast, an expression plasmid with a high copy number will be selected. Starting with high copy number plasmid overex-pressing the GPCR could be toxic to yeast and will result in greater variation in copy number among cells, resulting in different expression levels of GPCR from colony to colony and decreasing experimental reproducibility. Lastly, multiple yeast strains will be used to maximize the directed mutagenesis approaches.

Figure 5A:
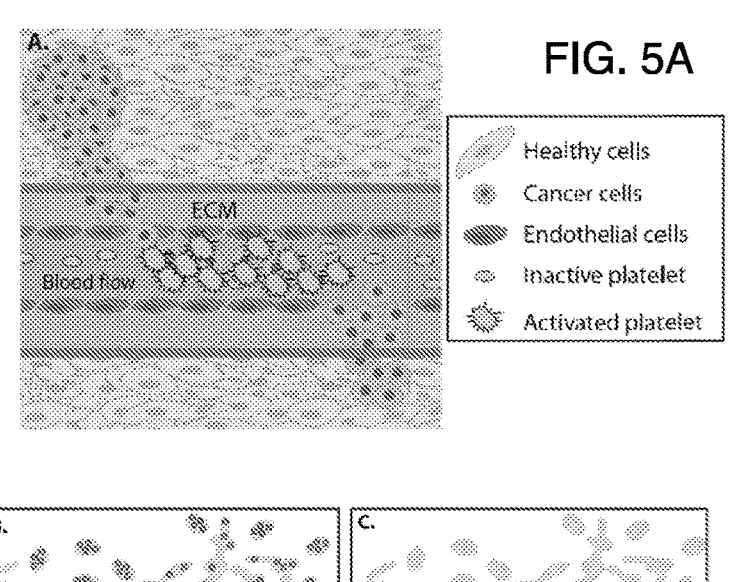
FIGS. 5A-C is an illustration showing engineered platelets for the targeted destruction of circulating tumor cells.

Example 4: Engineered Platelets for the Targeted Destruction of Circulating Tumor Cells Experiments were carried out to understand the therapeutic benefits of using platelets for preventing the spread of cancer, or metastasis. Metastasis is the main cause of cancer-associated mortality that occurs when some cancer cells, also called circulating tumor cells (CTCs), detach from primary tumor sites and enter the bloodstream to invade other tissues and organs at different locations (FIG. 5A). The presence of CTCs in patients is associated with a poor prognosis because once CTCs enter the bloodstream it is difficult to prevent them from reaching secondary organs and spreading cancer. Therefore, targeting CTCs may represent a target for anticancer therapies. The interaction of platelets and CTCs has been shown to influence metastasis as a result of both physical association, and bidirectional communication that causes platelet activation and CTC invasion, leading to metastatic colonization in distant locations from the primary tumor formation (Erpenbeck L, Schon M P. *Blood* 2010; 115(17): 3427-36; Labelle M, Hynes R O. *Cancer Discov* 2012; 2(12): 1091-9; and Stegner D, Dutting S, Nieswandt B. Mechanistic explanation for platelet contribution to cancer metastasis. *Thrombosis research* 2014; 133 Suppl 2: S149-57). Therefore, engineered platelets can serve as smart therapeutics for combatting metastasis in cancer patients.

Figures 5B, 5C:
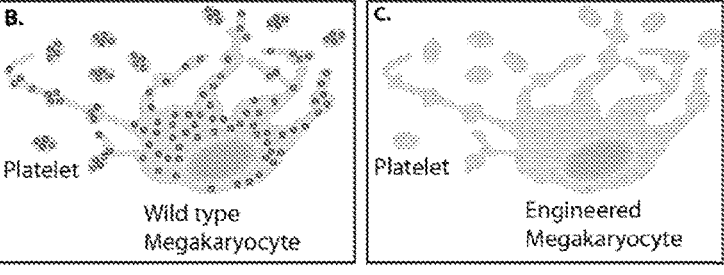

Disclosed herein are engineered pluripotent cells using approaches in synthetic biology to create engineered platelets that function as therapies for the targeted destruction of CTCs to prevent them from invading other organs and tissues. Platelets are typically filled with secretory granules that store large amounts of proteins, which are formed in the cytoplasm of megakaryocytes (MKs), their precursor cells (Deutsch V R, Tomer A. *British journal of haematology* 2006; 134(5): 453-66; and Machlus K R, Italiano J E, Jr. *The Journal of cell biology* 2013; 201(6): 785-96). Because platelets are cytoplasmic blebs made from extensions of MKs, they are filled with proteins present in the MK cytoplasm and do not contain a nucleus (FIG. 5B). Therefore, the exogenous DNA used in the precursor stem cells will not exist in the platelets, making this approach a practical therapeutic option for the targeted destruction of CTCs (FIG. 5C). Synthetic gene circuits, platelet engineering, and computational modeling can be used to develop gene networks in MKs that control when, where, and which cancer-specific receptors to target, thus reprogramming platelets with spatial and temporal control for targeting and killing CTCs. The backbone of the synthetic gene circuits will include an on/off cell fate switch that will enable the long-term expansion of MKs in vitro (ON state), and platelet production (OFF state) (Nakamura S, Takayama N, Hirata S, et al. *Cell Stem Cell* 2014; 14(4): 535-48) (FIG. 10A). The first class of synthetic gene networks to be built will permit the specific killing of CTCs through engineering monoclonal antibodies to target specific cancer receptors. The second class of synthetic gene networks to be built is a genetic tool that directs pluripotent stem cell fate to expand MKs, and the temporal control to load platelets with bioactive molecules during production of platelets. Altogether, these engineered platelets will enable the elimination of many CTCs that will significantly diminish or prevent metastasis. The therapies described herein can lead to increased flexibility, precision, and personalization. Furthermore, the genetic circuits and design principles described herein will serve as a general platform that can be combined with any tumor-specific receptors, and can be used to treat and/or manage many cancers. The technology described herein can combine cell-based immunotherapy and synthetic biology to cancer research to change existing cancer treatment.

Figures 7A, 7B:
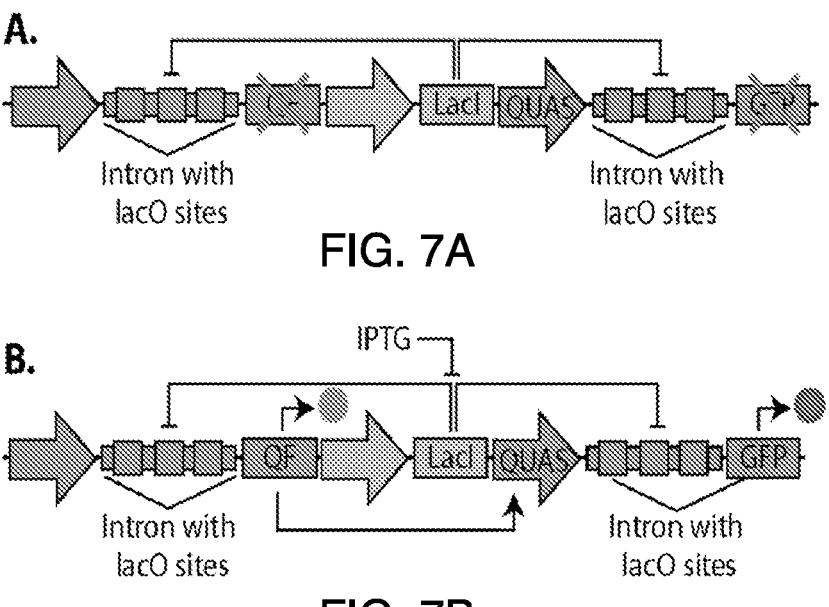
FIGS. 7A-B is a schematic of the LacQ genetic circuit.
Figure 8F:
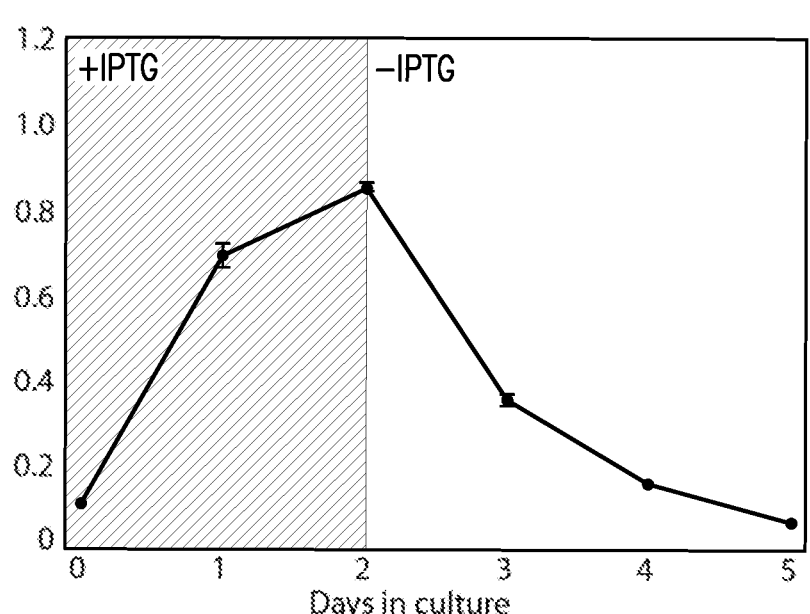

To this end, it has been demonstrated that these genetic tools can be used to tightly control gene expression in pluripotent stem cells (FIG. 7 and FIG. 8). For example, FIG. 7A shows that the Lad repressor proteins bind to the lac operator sites upstream of QF and GFP. This causes transcriptional repression of QF and GFP. As depicted in FIG. 7B, in the presence of IPTG, it binds to the Lad proteins and produces a conformational change in the repressor proteins. This causes the repressor proteins to no longer bind to the lac operator sites, allowing for the transcription of QF. Once QF proteins are produced, they bind to the QUAS binding sites and activate the transcription of GFP, resulting in a robust expression of GFP.

Engineering platelets to target and destroy circulating tumor cells. Cells are complex and dynamic systems that have the remarkable ability to continuously sense, integrate, store, and respond to these signals throughout their lives, making cell therapy an attractive avenue for next-generation cancer treatments. Platelets are attractive in cancer therapeutic settings for targeting CTCs because they commonly associate with CTCs, and many studies have shown that CTCs express a wide variety of receptors for attracting platelets to bind and, upon binding, promote their activation and release of their cellular contents (Lou X L, Sun J, Gong S Q, Yu X F, Gong R, Deng H. *Chin J Cancer Res* 2015; 27(5): 450-60; and Yu L X, Yan L, Yang W, et al. *Nature communications* 2014; 5: 5256). Synthetic biology has transformed how cells can be reprogrammed, providing a means to reliably and predictably control cell behavior with the assembly of genetic parts into more complex gene circuits (Weisenberger M S, Deans T L. *J Ind Microbiol Biotechnol* 2018; 45(7): 599-614). Megakaryocytes, the progenitor cells of platelets, are amenable to high-level reprogramming through synthetic biology. Disclosed herein are engineered blood platelets to be filled with inactive split toxins fused to monoclonal antibodies that specifically bind to CTC receptors. Once each half of the split toxin has been internalized by the CTC, the parts will spontaneously assemble to create a functional toxic protein and kill the cancer cell.

Disclosed herein are methods that use a synthetic biology approach to engineer the next generation of cancer therapy to target CTCs and combat metastasis with the goal to create a platform to produce programmed platelets for the destruction of CTCs. Specifically, genetic switching networks will be designed and constructed to drive the differentiation of pluripotent stem cells into MKs and tune the amount of split toxins to be loaded into the platelets. This will ensure the correct balance of loading and differentiation so that the artificial loading of split toxins does not interfere with platelet development. These split toxins will be engineered as part of synthetic monoclonal antibodies to target specific receptors known to be overexpressed CTCs for the targeted delivery of the split toxins. This approach allows for the targeting of CTCs using two different receptors, allowing for the cells that receive both inactive sides of the toxic protein to be killed and thus avoiding systemic toxicity. Moreover, through mathematical modeling and data derived from the characterization of the circuits and protein loading, design rules governing properties of these circuits in MKs will be delineated. These rules will provide an instruction manual on how to systematically design, build, and characterize new genetic tools for packaging therapeutic peptides into platelets from MK that will enable the adjustment of the performance of these circuits under various conditions; and systematically tune synthetic platelet activity.

Designing monoclonal antibodies with split toxic proteins to target CTCs. Discrimination between healthy cells and cancerous cells is an important characteristic for any successful cancer therapy. Monoclonal antibody-based treatment has been established as a promising therapeutic strategy for hematologic malignancies and solid tumors over the last 20 years, and over 30 monoclonal antibodies exist for tumor-associated antigens targeting by monoclonal antibodies, and some with FDA approval (Scott A M, Allison J P, Wolchok J D. *Cancer Immun* 2012; 12: 14). One type of monoclonal antibody in use includes antibodies that deliver a payload (e.g., drug, toxin, etc. that is covalently linked to the antibody) that leads to cell death. These antibodies are typically injected into patients and they bind directly to cancer cells. However, many of the so-called cancer-specific antigens that are overexpressed in cancer cells can also be found at lower levels in healthy cells, causing adverse side effects from these antibodies also binding to healthy cells. In an approach disclosed herein, because platelets are typically attracted to CTCs, they will bring the synthetic antibodies directly to the cancer cells, minimizing the opportunity for them to bind to healthy cells.

As a proof of concept to use split intein proteins in CTCs, split GFP (available from Addgene plasmid #70225 for N-terminal GFP with VMA intein and plasmid #70226 for C-terminal GFP with VMA intein) will be used as a reporter for response characterization. The N-terminal sequences of GFP and VMA intein will be encoded into the FC region of the HER2 antibody, which is used for targeting breast cancer cells (Scott A M, Allison J P, Wolchok J D. *Cancer Immun* 2012; 12: 14). HER2 positive metastatic breast cancer cells will be purchased from ATCC (#CRL2316, #CRL2320, or #CRL2343). Experiments can be run beginning with transfecting HeLa cells with both the N- and C-terminal GFP and VMA intein plasmids from Addgene using Lipofectamine (Invitrogen) to ensure that there is no GFP expression with just one half of the protein, and GFP expression is observed with both plasmids. Next, receptors will be designed to contain either the N- or C-terminal GFP or VMA inteins in the FC region of the HER2 antibody using standard molecular biology techniques (FIG. 7B). The FC region of the HER2 antibody will be engineered to have either N- or C-terminal split proteins in the FC region. Both versions of this antibody will be transfected into the breast cancer cells and GFP expression will be observed in cells that receive both the N- and C-terminal split protein antibodies. After determining GFP expression in the breast cancer cells, the N- and C-terminal GFP proteins will be exchanged for α-sarcin and cell death experiments will be conducted.

If the synthetic receptors are completely degraded in the lysosome before the inteins are able to reassemble a functional GFP protein, other methods of delivery will be investigated that include, for example, various viral coatings, different linkers for the split proteins, etc. If the receptors enter into the cells, but don't express GFP (qRT-PCR on the cell lysate will confirm this), different design strategies on the antibodies will be performed.

Figures 9A, 9B:
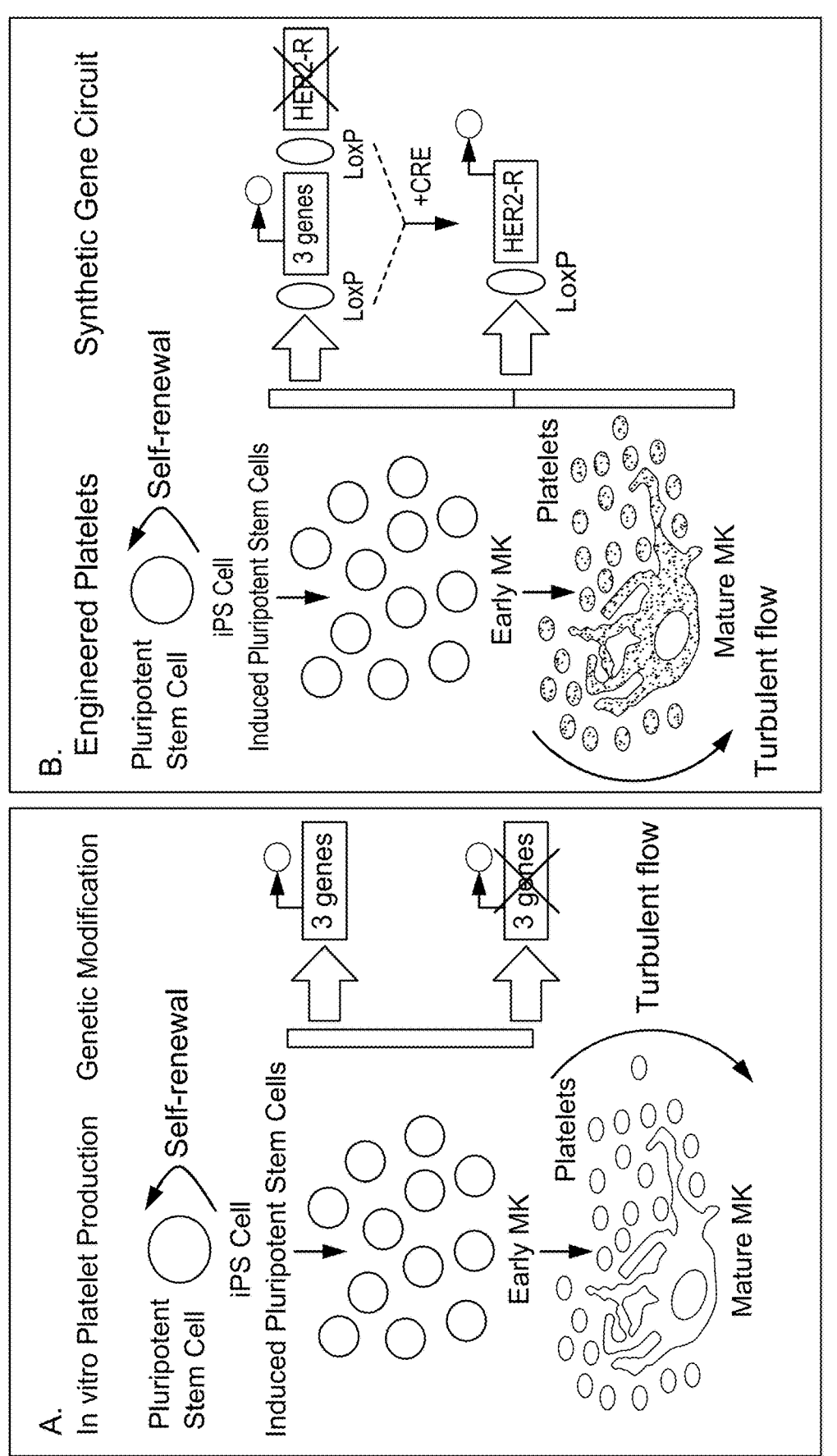
FIGS. 9A-B shows in vitro production of platelets.

Loading platelets with monoclonal antibodies that have split intein proteins. Using synthetic biology tools, MKs can be programmed to express therapeutic levels of protein cargo to be targeted for platelet secretion and the uptake by surrounding cancer cells. As a proof of concept, enhanced green fluorescence protein (EGFP), secreted alkaline phosphatase (SEAP), and luciferase will be expressed in MKs to determine the efficacy of using platelets as delivery vehicles for therapeutic payloads. This suite of reporter molecules has been selected because they can be used to assay different aspects of the cargo loading and delivery process. EGFP will be used to determine if soluble transgenic cargos are packaged into secretory granules, SEAP will be used to assay the extent of cargo release into the media of cells grown in vitro, and luciferase will be used to determine whether engineering platelets are enriched to sites of injury similar to endogenous platelets, to be used once these studies are moved to in vivo models. Recent studies have shown that immortalized MKs derived from human induced pluripotent stem (iPS) cells can be expanded by the overexpression of three genes (c-MYC, BMI1, and BCL-XL) for the expansion of early MKs, and when their expression is turned off, the cells mature and can produce platelets (Nakamura S, Takayama N, Hirata S, et al. *Cell Stem Cell* 2014; 14(4): 535-48; and Ito Y, Nakamura S, Sugimoto N, et al. *Cell* 2018; 174(3): 636-48). For platelet shedding, various turbulent flow-based bioreactors that maintain shear stress, as seen in the bone marrow, have been used (Ito Y, Nakamura S, Sugimoto N, et al. *Cell* 2018; 174(3): 636-48; Avanzi M P, Oluwadara O E, Cushing M M, Mitchell M L, Fischer S, Mitchell W B. Transfusion 2016; 56(1): 170-8; Blin A, Le Goff A, Magniez A, et al. *Sci Rep* 2016; 6: 21700; Di Buduo C A, Wray L S, Tozzi L, et al. *Blood* 2015; 125(14): 2254-64; Nakagawa Y, Nakamura S, Nakajima M, et al. *Exp Hematol* 2013; 41(8): 742-8; and Thon J N, Montalvo A, Patel-Hett S, et al. *The Journal of cell biology* 2010; 191(4): 861-74) (FIG. 9A). To engineer platelets to target and destroy CTCs, genetic circuits will be built to produce bioactive proteins in MKs that will be loaded into platelets as they mature (FIG. 9B). To accomplish this, the three genes used for MK proliferation will be flanked by LoxP sites, and the gene for the desired bioactive protein to be loaded into platelets will be placed downstream of the second LoxP site. In the absence of Cre recombinase, the three genes remain on to promote MK proliferation, however, once Cre recombinase is added to the cells (via transient transfection using Lipofectamine or viral induction), this will cause the DNA to undergo homologous recombination and cut out the three genes that are flanked by the LoxP sites. This turns on the downstream gene for the protein to be loaded into the platelets. Initial experiments will use GFP to easily assess and characterize the expression in MKs and the loading of the protein into platelets.

If GFP is not expressed in platelets, myristol-tagged GFP, that has been shown to associate with the cell membrane (Rhee J M, Pirity M K, Lackan C S, et al. *Genesis* 2006; 44(4): 202-18), will be used. In this case, the GFP will associate with the M K membrane and is likely to become a part of the platelet membrane. Microscopy and flow cytometry will be done to observe and quantify GFP expression. If SEAP or luciferase are not a part of the platelets, these reporter genes can be tagged with the amino acid sequence, LKNG (SEQ ID NO: 1), which has been demonstrated to be directly involved in the targeting and/or storage of the megakaryocytic proteins (El Golli N, Issertial O, Rosa J P, Briquet-Laugier V. The *Journal of biological chemistry* 2005; 280(34): 30329-35). To accomplish this, the LKNG (SEQ ID NO: 1) sequence can be fused to the reporter molecules in either the 5' or 3' UTR to be targeted for granule packaging in MKs.

Killing tumor cells with loaded platelets. Platelets associate with CTCs in the blood stream and play a role in metastasis by promoting platelet activation and tumor cell signaling (Erpenbeck L, Schon M P. *Blood* 2010; 115(17): 3427-36; Gay L J, Felding-Habermann B. *Nat Rev Cancer* 2011; 11(2): 123-34; Li N. Platelets in cancer metastasis: To help the "villain" to do evil. *Int J Cancer* 2016; 138(9): 2078-87; Borsig L. *Expert Rev Anticancer Ther* 2008; 8(8): 1247-55; Honn K V, Tang D G, Crissman J D. Platelets and cancer metastasis: a causal relationship? *Cancer Metastasis Rev* 1992; 11(3-4): 325-51; Ward Y, Lake R, Faraji F, et al. Platelets Promote Metastasis via Binding Tumor CD97 Leading to Bidirectional Signaling that Coordinates Transendothelial Migration. *Cell Rep* 2018; 23(3): 808-22; and Yu L X, Yan L, Yang W, et al. Platelets promote tumour metastasis via interaction between TLR4 and tumour cell-released high-mobility group box1 protein. *Nature communications* 2014; 5: 5256). Initial experiments will create loaded platelets using a WAVE bag system to provide turbulent flow for platelet shedding (Ito Y, Nakamura S, Sugimoto N, et al. Turbulence Activates Platelet Biogenesis to Enable Clinical Scale Ex Vivo Production. *Cell* 2018; 174(3): 636-48). Indeed, this method will not produce clinically relevant numbers of platelets, but it will allow small scale harvesting of engineered platelets to test on metastatic breast cancer cell lines. Next, the platelet production can be scaled up by using the new VerMES bioreactor that has been shown to provide optimal turbulence, vorticity, and shear to produce clinically relevant numbers of platelets (Ito Y, Nakamura S, Sugimoto N, et al. *Cell* 2018; 174(3): 636-48). To investigate the effect of the engineered platelet interactions with tumor cells, the ability of the breast cancer cells to stimulate aggregation and activation of the engineered platelets around the cancer cells will be measured, in addition to the uptake of the secreted bioactive proteins from the ruptured platelets and their translocation into the cancer cells will be monitored. Experiments will also monitor the movement of GFP on the engineered receptors from the platelets to the tumor cells. Once GFP is observed in the tumor cells, GFP will be replaced with α-sarcin. Tumor cell death will be measured with live-dead assays and population counts.

By using iPS cells to create MKs, and genetically modifying the MKs to mass-produce desired bioactive proteins to be packaged into platelets for targeted delivery, this allows the therapy to benefit more patients, yet to remain highly personalized.

---

---

What is claimed is:

1. A nucleic acid construct comprising:

a) a promoter operatively linked to a sequence encoding c-MYC, BMI1, and BCL-XL; and b) a sequence encoding an engineered antibody sequence, wherein the engineered antibody sequence comprises a split toxin sequence flanked by an intein sequence;

wherein the sequence encoding c-MYC, BMI1, and BCL-XL is flanked by a first recombination site and a second recombination site;

wherein the sequence encoding the engineered antibody sequence is out of frame from the promoter;

wherein, when exposed to a recombinase under conditions suitable to catalyze a site-specific recombination event between the first recombination site and the second recombination site, the sequence encoding c-MYC, BMI1, and BCL-XL is excised and the sequence encoding the engineered antibody sequence is brought in frame with the promoter.

2. The nucleic acid construct of claim 1, wherein the promoter is CMV, RSV, U6, beta actin, or elongation factor promoter.

3. The nucleic acid construct of claim 1, wherein the first or second recombination sites are loxP, attP or Bxb1 recombination sites.

4. The nucleic acid construct of claim 1, wherein the promoter is a regulatable promoter.

5. The nucleic acid construct of claim 1, wherein the engineered antibody sequence comprises a split toxin sequence flanked by an intein fragment, wherein the intein fragment comprises an intein N-fragment, wherein the split toxin sequence is N-terminal to an intein N-fragment.

6. The nucleic acid construct of claim 1, wherein the engineered antibody sequence comprises a split toxin sequence flanked by an intein fragment, wherein the intein fragment comprises an intein C-fragment, wherein the split toxin sequence is C-terminal to an intein C-fragment.

7. A megakaryocyte comprising the nucleic acid construct claim 1.

8. A method of producing a platelet comprising an engineered antibody, the method comprising:

a. providing pluripotent stem cells comprising the nucleic acid construct of claim 1;

b. culturing the pluripotent stem cells in a media under conditions to permit the expansion of the pluripotent stem cells to megakaryocytes;

c. exposing the megakaryocytes to a recombinase under conditions suitable to catalyze a site specific recombination event between the first recombination site and the second recombination site, thereby excising the sequence encoding c-MYC, BMI1, and BCL-XL, and bringing the sequence encoding the engineered antibody sequence in frame with the promoter, and d. differentiating the megakaryocytes into platelets;

wherein the platelets comprise the engineered antibody encoded by the engineered antibody sequence.

9. The method of claim 8, wherein the engineered antibody comprises:

a. an Fc region that comprises a split toxin sequence flanked by an intein fragment, wherein the intein fragment comprises an intein N-fragment, and wherein the split toxin sequence is N-terminal to an intein N-fragment;

b. an Fc region comprising a split toxin sequence flanked by an intein fragment, wherein the intein fragment comprises an intein C-fragment, and wherein the split toxin sequence is C-terminal to an intein C-fragment; or c. a first Fc region comprising a first split toxin sequence flanked by a first intein fragment, wherein the first intein fragment comprises an intein N-fragment, wherein the first split toxin sequence is N-terminal to the intein N-fragment, and a second Fc region comprising a second split toxin sequence flanked by a second intein fragment, wherein the second intein fragment comprises an intein C-fragment, wherein the second split toxin sequence is C-terminal to the intein C-fragment.

10. The method of claim 8, wherein the promoter is a regulatable promoter.

11. The method of claim 10, wherein the media comprises isopropyl β-D-1-thiogalactopyranoside (IPTG).

12. The method of claim 9, wherein the Fc region or the first Fc region and the second Fc region are Fc regions of an IgG antibody or fragment thereof, and wherein the IgG antibody or fragment thereof is an anti-Her-2 antibody.

* * * * *